(12) United States Patent
Mabe Alvarez

(10) Patent No.: US 10,473,577 B2
(45) Date of Patent: Nov. 12, 2019

(54) MONITORING SYSTEM AND METHOD FOR DETECTING FLOWING MICROSCOPIC OBJECTS

(71) Applicant: ATTEN2 ADVANCED MONITORING TECHNOLOGIES S.L., Eibar (ES)

(72) Inventor: Jon Mabe Alvarez, Eibar (ES)

(73) Assignee: ATTEN2 ADVANCED MONITORING TECHNOLOGIES S.L., Eibar (ES)

( * ) Notice: Subject to any disclaimer, the term of this patent is extended or adjusted under 35 U.S.C. 154(b) by 0 days.

(21) Appl. No.: 15/867,213

(22) Filed: Jan. 10, 2018

(65) Prior Publication Data

US 2018/0195949 A1 Jul. 12, 2018

(30) Foreign Application Priority Data

Jan. 11, 2017 (EP) .................................... 17382007

(51) Int. Cl.
*G01N 15/14* (2006.01)
*G02B 21/06* (2006.01)
(Continued)

(52) U.S. Cl.
CPC ..... *G01N 15/1434* (2013.01); *G01N 15/0227* (2013.01); *G01N 15/1429* (2013.01);
(Continued)

(58) Field of Classification Search
CPC ....... G01N 2015/1006; G01N 15/1434; G01N 15/1459; G01N 15/1404; G01N 15/1425;
(Continued)

(56) References Cited

U.S. PATENT DOCUMENTS 4,136,950 A * 1/1979 Labrum ............. G01N 15/0205
250/222.2
2006/0001860 A1* 1/2006 Scibona .............. A61M 1/3693
356/39

FOREIGN PATENT DOCUMENTS

CN 2899386 5/2007
EP 0507746 10/1992
(Continued)

OTHER PUBLICATIONS

Extended Search Report for European Patent Application No. 17382007.7, dated Aug. 1, 2017, 11 pages.

*Primary Examiner* — Michael P Stafira
(74) *Attorney, Agent, or Firm* — Sheridan Ross P.C.

(57) ABSTRACT

A system (1) for detecting microscopic objects located in a flowing fluid. It comprises a lighting system (205, 305) comprising at least one LED diode (605) for supplying light to the flowing fluid; an image capture system (201, 601) configured to capture a sequence of images of the fluid. The image capture system comprises a camera comprising a plurality of pixels. The sequence of images is processed and the presence and shape of microscopic objects is determined. The lighting system (205, 305) is configured to supply high power light pulses having amplitude Io' and very short time duration $T_{ON}$, the time instant at which said pulses are triggered being synchronized with the time instants at which pixels in the image capture system (601) start to capture an image frame. The amplitude Io' and time duration $T_{ON}$ of the light pulses are controlled by calculating, from the light intensity ($I_{frame}$) of each captured image frame, a pulse amplitude setpoint (PAS) and a pulse duration setpoint (PDS) for adjusting respective potentiometers (651, 652) configured to respectively fix the amplitude Io' and pulse duration $T_{ON}$ by executing an algorithm that prioritizes amplitude rises over pulse duration rises. The lighting sys- (Continued)

tem (305) comprises an energy loading system (670) configured to make the amplitude requirement and response time of the lighting system (305) independent from the power supply unit. Method for detecting microscopic objects suspended in a flowing fluid.

20 Claims, 11 Drawing Sheets

(51) Int. Cl.
G03B 15/02 (2006.01)
G01N 33/28 (2006.01)
G02B 21/36 (2006.01)
G01N 15/02 (2006.01)
H04N 5/235 (2006.01)
H05B 33/08 (2006.01)

(52) U.S. Cl.
CPC ......... *G01N 33/2835* (2013.01); *G02B 21/06* (2013.01); *G02B 21/361* (2013.01); *G03B 15/02* (2013.01); *H04N 5/2354* (2013.01); *G01N 2201/0696* (2013.01); *H05B 33/0845* (2013.01)

(58) Field of Classification Search
CPC ........... G01N 2015/1497; G01N 15/12; G01N 15/1245; G01N 15/1463; G01N 15/147; G01N 15/1475; G01N 15/1484; G01N 2015/1075; G01N 2015/1409; G01N 2015/1477; G01N 2015/1486; G01N 2015/1495; G01N 21/1702; G01N 21/39; G01N 2201/0697; G01N 27/02; G01N 33/56972; G01N 15/0205; G01N 15/0211; G01N 15/0227; G01N 15/1429; G01N 15/1436; G01N 1/30; G01N 1/34; G01N 1/38; G01N 1/4044; G01N 1/42; G01N 1/44; G01N 2001/4094; G01N 2015/0065; G01N 2015/1413; G01N 2015/1452; G01N 2015/149; G01N 21/0303; G01N 21/76; G01N 21/763; G01N 2201/0696; G01N 2333/726; G01N 2333/90241; G01N 2500/20; G01N 33/2835; G01N 33/4833; G01N 33/48728; G01N 33/5008; G01N 33/5308; G01N 33/542; G01N 33/569; G01N 33/573; G01N 33/581; G02B 21/361; G02B 21/06; G02B 21/34
See application file for complete search history.

(56) References Cited

FOREIGN PATENT DOCUMENTS

| EP | 1533996 | 5/2005 |
|----|---------|--------|
| EP | 2602608 | 6/2013 |
| EP | 2980557 | 2/2016 |

* cited by examiner

MONITORING SYSTEM AND METHOD FOR DETECTING FLOWING MICROSCOPIC OBJECTS

CROSS REFERENCE TO RELATED APPLICATIONS

This application claims the benefit of Europe Patent Application No. EP17382007.7 filed 11 Jan. 2017, the disclosure of which is incorporated herein by reference.

TECHNICAL FIELD

The present invention relates to the field of fluid monitoring for determining the general condition of fluids, such as their degradation and particle content. This monitoring is for example applicable to lubricating oils, since their state of degradation and particle content provides information on the machinery lubricated by said oil.

BACKGROUND OF THE INVENTION

Industrial machines often undergo unforeseen shutdowns and failures, often associated to aspects related to lubrication. Lubricating oil is one of the key components in some of these machines and provides a lot of information regarding the machines condition. It may be interesting to monitor some parameters in lubricating oil, such as particle determination (for example, quantification, classification of size or determination of shape), bubble content in the system or oil degradation based on colour. Oil degradation is a key indicator of oil quality and how it fulfils its lubricating mission. It does not provide information on the machine directly, but indirectly, from the speed of degradation, it is possible to extract information regarding the machine's operation.

European patent application EP2980557A1 discloses a system for inspecting oil, which comprises a cell through which oil flows along a pipe. The system is based on a lighting system having a LED diode, configured to supply a light beam to the flow of oil, and an image capture system situated on the opposite side of the pipe in respect of the lighting system. The image capture system is configured to capture a sequence of images of the oil that flows inside the pipe. The lighting system and the image capture system are disposed within the cell. A processor processes the sequence of images and determines the presence of particles and a value for the oil degradation.

The system disclosed in EP2980557A1 performs as expected when the oil, and therefore the particles comprised therein, travel along the pipe at low speed. However, it has been observed that when the instant velocity of the particles is relatively high, when they pass by the area of image capture, the system is unable to capture an image of the passing particles or it manages to capture an image in which the particles have an incorrect morphology. This has for example been observed for particles travelling with instant velocity varying between 3 and 20 m/s (the smaller the particle, the lower the threshold of instant velocity above which the particle is not captured in the image or it is captured with incorrect morphology).

Capturing undistorted images of objects moving at relatively high speed at the image capture area is a traditional problem. If the sampling rate of each pixel is not fast enough, the captured images will tend to be blurry and with shapes that do not correspond to reality. The sampling rate of each pixel depends mainly on two factors: the exposure time (the time for which each pixel collects the instant light that comes to it) and the reading time of each pixel (the maximum rate at which information from each pixel in the camera is transferred to a buffer). The capture of images on very dark oils can be compensated with an increase of the exposure time or with an increase of the intensity on the lighting source. While the exposure time is dependent on each application and is a function of the maximum illumination power available and of the opacity of the fluid to be analyzed, the reading time of each pixel depends on the technology of the video sensor.

Indeed, the problem of moving objects can be avoided by mechanical means using devices for flow regulation (in order to reduce the flow speed) or solenoid valves for stopping the oil sample under analysis. However, stopping or reducing the fluid flow rate directly impacts of the significance of the measurement, because samples are not being taken in real conditions. Flow regulators, such as needle valves for instance, tend to filter particles by themselves and can be easily stoppled by the accumulation of wear debris in highly contaminated fluids (like the ones targeted in the present invention) and the valves only allow the measurement of static samples with no flow at all, which impacts in the sampling speed and in the representativeness of the sample. Ideally, reducing the number of hydraulic elements enhances the measurement significance of an in-line or by-pass sensor.

Besides, certain techniques have been developed for overcoming the problem of capturing images of moving objects at the image capture area. One of the traditional techniques is called Rolling Shutter (RS). In RS, the pixels are activated sequentially one after the other. The temporal difference of the activation of a pixel with the forthcomings causes the captured images to appear moved and not focused if the objects move faster than the reading speed of each pixel. Another technique is called Global Shutter: This technology allows all pixels to be activated simultaneously, so regardless of the speed of the object to be captured, it appears static in the captured image. A third technique is called Rolling Shutter with Global Start (RSGS): This technology is a particular case of the Rolling Shutter, and allows all the pixels to be activated at the same instant, although the duration of the activation depends on the reading instant of each one, which is still sequential, which causes that some pixels are active longer than others.

However, in order to apply these techniques to the detection of microscopic particles comprised in a moving fluid, some parameters must be considered: (a) the resolution of the detector (height×width in pixels), (b) the pixel size and (c) the sensor area, because these three parameters determine (1) the minimum detectable size of a particle (which is dependent on the ratio between resolution and pixel size) and (2) the volume of analyzed fluid in each image (which is dependent on the sensor's active area). For this reason, Global Shutter techniques are discouraged for the detection of small particles in a moving fluid because in the state of the art solutions, due to their higher complexity in the pixel structure, they tend to offer lower resolutions and larger pixel sizes. Besides, even if Rolling Shutter solution is able to offer decent resolutions, pixel sizes for this specific application are not an option due to their limitations for capturing sharp images of moving objects. On the contrary, RSGS allows maintaining the advantages of the RS sensors while offering a performance in the capture of moving objects similar to the GS, under certain conditions, such as the isolation of CMOS detector of the non-controlled light sources (e.g. ambient lighting).

Nevertheless, when applying traditional RSGS setups to the detection of particles in a moving fluid, it has been observed that the system does not perform as expected for two reasons: (1) the image capture system does not receive enough light power (flash gain), which is normally required for the images and particles suspended on the fluid to have enough contrast in order to enable their discrimination; and (2) the time for which the lighting system is on (flash duration) is too elevated and therefore the images are not captured in a clear way.

Chinese patent application CN2899386 discloses a LED-array source for inspecting a printing image, in which the LED source provides a pulsed signal synchronized with the image printing speed. In order to synchronize the pulse signal with the printing speed, a circuit is designed for adjusting the frequency of the pulse signal. However, this disclosure does not give any clue regarding as how to provide very high power pulses from a conventional low current DC power source. Additionally, in systems for inspecting a moving fluid, the light pulses cannot be synchronized with the particle velocity because the inspection system does not know this velocity.

Therefore, there is a need for a system for inspecting a moving fluid which overcomes the former drawbacks.

DESCRIPTION OF THE INVENTION

The present invention attempts to solve the drawbacks mentioned above by means of a monitoring system and method for detecting microscopic objects disposed in a flowing fluid. The microscopic objects flow at high flow rates. In the context of the present invention, the term "high" in "high flow rates" refers to flow rates varying between 1 and 40 m/s, that is to say, flow rates of up to 40 m/s. The monitoring system uses a pulsed lighting system, that is to say, a lighting system that produces regular flashes of light, synchronized with the video capturing speed. In the context of the present invention, the term "microscopic" refers to objects having a largest dimension (i.e. diameter) smaller than 20 μm. The monitoring system of the invention has been proved to detect and correctly identify objects in motion (objects suspended in a flowing fluid) having a largest dimension smaller than 10 μm and even smaller than 3 μm when they move at instant velocity of 20 m/s. The pulsed lighting system ensures that the light it provides is on (flash duration) in a controlled way, in particular for a shorter time than the exposure time selected in the sensor (i.e. CMOS) of the image capture system, since in that way, once the light source is turned off, even if there are still active pixels (until the exposure time is finished) the active pixels will have no effect, since there are no more photons to be received (the CMOS is isolated from any external light source). Besides, the lighting system is synchronized with the image capture system to trigger the flash pulses at the beginning of every new video frame. What is more, the system is designed for the image capture system to receive enough flash gain so as to correctly discriminate particles within the moving fluid. In this context, the exposure time is the time for which each pixel collects the instant light that comes to it and it is limited in practice by the duration of the flash pulse.

As mentioned earlier, because the monitoring system is isolated from outside light (the only light source is that of the monitoring system) and the lighting system allows a total shutdown, applying the RSGS technique is possible.

Therefore, the system and method for inspecting a fluid manages to perform correctly without needing to actuate on the speed of the fluid flow. In other words, the system of the invention is capable of capturing images of the passing particles in continuous flow and of determining the real size and shape of the microscopic objects shown in the captured images (and not a distorted version of the objects).

In a first aspect of the invention, a system is provided for detecting microscopic objects located in a flowing fluid. The system comprises: a lighting system comprising at least one LED diode and configured to supply light to the flowing fluid; an image capture system situated on the opposite side of the flowing fluid in respect of the lighting system, the image capture system being configured to capture a sequence of images of the flowing fluid, the image capture system comprising a camera in turn comprising a plurality of pixels; processing means configured to process the sequence of images and to determine the presence of microscopic objects within the flowing fluid and the shape of the microscopic objects. The lighting system is configured to supply high power light pulses having amplitude Io' and very short time duration $T_{ON}$. In the context of the present invention, the term "high" in "high power light pulses" refers to power pulses varying between 20 mA and 20 A, preferably between 2 A and 15 A. In the context of the present invention, the expression "very short" in "very short time duration" refers to time duration varying between 50 ns and 50 μs, preferably between 50 ns and 20 μs, more preferably between 50 ns and 10 μs, and still more preferably varying between 50 ns and 5 μs. The time instant at which these pulses are triggered is synchronized with the time instants at which pixels in the image capture system start to capture an image frame. The processing means is configured to control the amplitude Io' and time duration $T_{ON}$ of the light pulses supplied by the lighting system by means for calculating, from the light intensity $I_{frame}$ of each captured image frame, a pulse amplitude setpoint (PAS) and a pulse duration setpoint (PDS) for adjusting respective potentiometers configured to respectively fix the amplitude Io' and pulse duration $T_{ON}$. The means for calculating the pulse amplitude setpoint (PAS) and the pulse duration setpoint (PDS) is configured to execute an algorithm that prioritizes amplitude rises over pulse duration rises. The lighting system also comprises an energy loading system configured to make the amplitude requirement and response time of the lighting system independent from a power supply unit of the system.

Preferably, the image capture system operates in RSGS mode.

In embodiments of the invention, the image capture system is configured to provide the processing means with an image frame captured every $T_{frame}$ seconds, $T_{frame}$ being less than or equal to $T_{EXP}$, wherein $T_{EXP}$ is the exposure time of the pixels comprised in the image capture system.

In embodiments of the invention, the lighting system comprises a pulse generator for generating from the pulse duration setpoint (PDS) and from a strobe signal provided by the image capture system, a pulsed signal having period $T_{frame}$ and having pulses of duration $T_{ON}$, $T_{ON} \ll T_{EXP} \leq T_{frame}$, the duration $T_{ON}$ being obtained from the pulse duration setpoint (PDS) and said strobe signal being used for synchronizing the pulses of duration $T_{ON}$ with the time instant at which the pixels in the image capture system start to capture an image frame. In a particular embodiment, the pulse generator is implemented with a single retriggerable monostable forming, together with the potentiometer adjustable by the pulse duration setpoint (PDS), an RC network configured to fix the pulse duration $T_{ON}$.

In embodiments of the invention, the lighting system further comprises a multiplexor configured to provide a reference voltage $V_{MUX}$ of duration $T_{ON}$, and a substantially null voltage of duration $T_{frame}$–$T_{ON}$, wherein the reference voltage $V_{MUX}$ is calculated from the pulse amplitude setpoint (PAS) obtained at processing means, the reference voltage $V_{MUX}$ being used for obtaining a polarization current of the at least one LED.

In embodiments of the invention, the energy loading system comprises a switched-mode power supply configured to provide a voltage $V_{int}$ and a low current $I_{int}$ from a DC power supply source $V_{out}$; and an RC network comprising at least one capacitor and a resistor, wherein the at least one capacitor works as a pulse energy storage means and the resistor regulates the charging speed of the pulse energy storage means. The RC network is configured for the at least one capacitor to become fully charged in a time duration $T_{frame}$–$T_{ON}$, wherein $T_{frame}$ is the time period between two consecutive image frames captured by the image capture system, the switched-mode power supply thus providing a voltage $V_{LED}$ in turn enabling to provide the at least one LED with current Io'.

In embodiments of the invention, the system further comprises a diffuser situated between the lighting system and the flow of fluid, configured to provide homogeneous lighting to the area to be illuminated.

In embodiments of the invention, the diffuser is situated closing off and sealing a hole made in the pipe through which the fluid flows.

In embodiments of the invention, the system further comprises a lens situated between the image capture system and the flow of fluid, configured to focus the captured images.

In embodiments of the invention, the system further comprises a calibration device situated between the lens and the flow of fluid.

In embodiments of the invention, the processing means is configured to determine the presence and shape of objects having a largest dimension smaller than 20 μm.

In embodiments of the invention, the light pulses supplied by the lighting system have amplitude Io' varying between 20 mA and 20 A and time duration $T_{ON}$ varying between 50 ns and 50 μs.

In another aspect of the invention, a method for detecting microscopic objects located in a flowing fluid is disclosed. It comprises: supplying light emitted by at least one LED to a flowing fluid having microscopic objects suspended thereon; capturing a sequence of images of the flowing fluid by means of an image capture system comprising a plurality of pixels; processing the sequence of images and determining the presence of microscopic objects within the flowing fluid and the shape thereof; at the image capture system, capturing an image frame every $T_{frame}$ seconds, $T_{frame}$ being higher than or equal to $T_{EXP}$, wherein $T_{EXP}$ is the exposure time of the pixels comprised in the image capture system; providing a strobe signal the said image capture system; for each image frame, calculating (controlling) a pulse amplitude setpoint (PAS) and a pulse duration setpoint (PDS) from the intensity of each frame $I_{frame}$ by executing an algorithm that prioritizes rises in the pulse amplitude (PAS) rather than rises in the pulse duration (PDS); at a pulse generator (655), receiving the pulse duration setpoint (PDS) and generating from the pulse duration setpoint (PDS) and from the strobe signal a pulsed signal having period $T_{frame}$ and having pulses of duration $T_{ON}$, $T_{ON} \ll T_{frame}$, the duration $T_{ON}$ being obtained from the pulse duration setpoint (PDS) and the strobe signal being used for synchronizing the pulses of duration $T_{ON}$ with the time instant at which the pixels in the image capture system start to capture an image; calculating a reference voltage $V_{MUX}$ of duration $T_{ON}$ from the pulse amplitude setpoint (PAS), the reference voltage $V_{MUX}$ being used for obtaining a polarization current of the at least one LED; providing a voltage $V_{LED}$ enabling to provide a current Io' to the at least one LED at pulses of duration $T_{ON}$, the voltage $V_{LED}$ being provided by an RC network comprising at least one capacitor and a resistor, wherein the at least one capacitor works as a pulse energy storage means and the resistor regulates the charging speed of the pulse energy storage means, the RC network being configured for the at least one capacitor to become fully charged.

In embodiments of the invention, the stage of, for each frame, calculating a pulse amplitude setpoint (PAS) and a pulse duration setpoint (PDS) from the intensity of each frame ($I_{frame}$), is done as follows: from current PAS, PDS and luminance generated with the PAS and PDS, checking whether the current luminance is within a design range $LUMA_{MIN}$<current LUMA<$LUMA_{MAX}$; if $LUMA_{MIN}$<current LUMA<$LUMA_{MAX}$, then no control is required; otherwise, it is checked whether the time duration of the deviation with respect to the established range ($LUMA_{MIN}$, $LUMA_{MAX}$) is larger than a design hysteresis time and if the current luminance is out of the design range for a time duration shorter than the defined hysteresis time, then no control is required; otherwise, it is checked whether or not the current pulse amplitude setpoint PAS corresponds to a maximum value of intensity and, if not, then the following calculation is performed: new_PAS=($I_{frame}$–$I_{frame\_setpoint}$)× Gain_PAS, the new_PAS value being used to update said potentiometer; if the current pulse amplitude setpoint PAS corresponds to a maximum value of intensity, the pulse duration is adjusted as follows: new_PDS=($I_{frame}$ –$I_{frame\_setpoint}$)×Gain_PDS, the value of new_PDS being used to update said potentiometer.

In another aspect of the invention, a computer program comprising computer program code means adapted to perform the steps of the previous method is provided when the program is run on a computer, a digital signal processor, a field-programmable gate array, an application-specific integrated circuit, a micro-processor, a micro-controller, or any other form of programmable hardware.

In sum, the proposed system and method permits to work with conventional DC voltage sources of very low current, in spite of the fact that the light pulses illuminating the fluid under inspection are of very high current. With the proposed system and method, for example a conventional 24 VDC and 1 mA power source is enough to feed pulses of 6 A and duration of 4 μs at frequencies of for example 1 KHz. This enables to operate with any conventionally available power supply, normally not able to directly feed power for high current (e.g. 6 A) short pulses (4 μs) due to their switching on and off ramp times.

A collateral advantage of the system of the invention is the elimination of the need to control the light source in order to dampen the efficiency changes of the light source as a function of temperature, because the light source does not self-heat as it works in small duty cycles (<1%).

Additional advantages and features of the invention will become apparent from the detail description that follows and will be particularly pointed out in the appended claims.

BRIEF DESCRIPTION OF THE DRAWINGS

As a complement to the description and with a view to contributing towards an improved understanding of the characteristics of the invention, according to an example of a practical example thereof, a set of drawings is attached as an integral part of this description, which by way of illustration and not limitation, represent the following.

DESCRIPTION OF AN EMBODIMENT OF THE INVENTION

Figure 1:
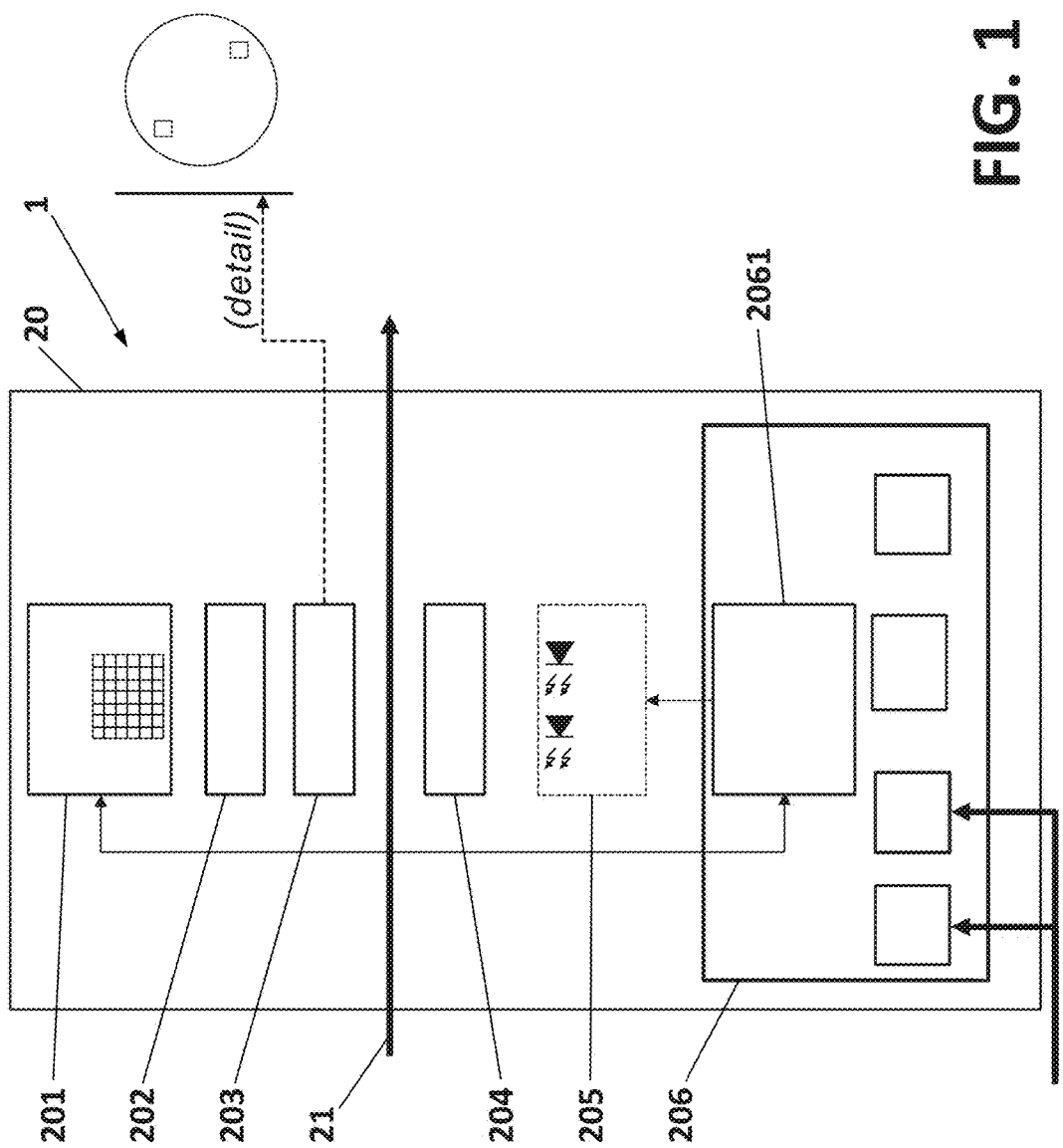
FIG. 1 represents a general outline of the monitoring or inspection system according to an embodiment of the invention.

FIG. 1 represents a general outline of a monitoring or inspection system 1 according to an embodiment of the invention. At the monitoring system 1 measurements of a moving fluid are taken. This system 1 has been conceived as an autonomous system with totally independent functioning, which delivers auto interpretable measurements, calibrated and corrected for the entire defined operating range. In other words, the measurement system 1 delivers measurement values that have no need of further processing. The system is specifically designed for its direct integration into the lubricating systems of machinery without affecting the operating conditions thereof. This is achieved by means of hydraulic piping (not shown) which make it possible to carry out controlled sampling in lubricating fluid (for example, oil) either by by-pass or by in-line installation. Communication interfaces and power supply units are also used in order to carry the system's results to the machine in question or wherever required. It is remarked that any conventional low current power source (such as, but not limiting, a conventional power source of 24 V (DC) and current of 1 mA) suffices for powering the proposed system, in spite of the lighting system requiring to be fed with pulses having (for example 6 A (current) and extremely short duration (for example around 4 μs) in frequencies of around 1 kHz. This is enabled by means of the proposed driving circuit for the lighting system, which is described in detail later in this text.

The system 1 must have a small size and be as compact as possible to be fitted within larger hydraulic subsystems, such as filters or valves. The measurement system 1 operates on a micromechanical cell 20 through which the fluid 21 under supervision circulates. In a preferred embodiment, this fluid is oil, more preferably lubricating or hydraulic oil. The fluid 21 is driven inside channelling means, such as for example a regular pipe and circulates thanks to a small pressure difference between the input and the output of the system (0.05 Bar or larger is enough).

The measurement system 1 comprises an optical part and an electronic part (or video acquisition and processing sub-system). The video acquisition and processing sub-system carries out the activities related to measurements, among other things. It is made up of an embedded image capture system 201 and by electronics 206 comprising processing means 2061. The measurement system 1 is based on an embedded artificial vision measurement system, wherein by means of an image capture system 201 a video sequence is captured which is processed in processing means 2061, such as an embedded processor. In some embodiments of the invention, the processing means 2061 is a DSP device (Digital Signal Processor) or a CPU (Central Processing Unit). The goal of the processing is to determine the presence of particles and/or bubbles and the degradation value of the fluid (for example, oil)-and to determine the shape of the particles. For this purpose, processing means 2061 comprises software means, formed by a group of algorithms for the detection and classification of particles, bubble detection and determination of degradation. The arrow connecting the image capture system 201 and the processing means 2061 outlines the video data and control lines.

The image capture system 201 is configured to work in RSGS mode. In a possible embodiment, an acquisition and processing system of 4 frames per second (4 FPS) is used. For example, a 5 Mpix On Semiconductor device can be used.

The optical part comprises a lighting system 205 to subject the flow of fluid 21 to a beam of light, in such a way that the image capture system 201 captures a video sequence that will afterwards be processed in the processing means 2061. The lighting system 205 is designed to supply a pulsed beam of white light to the fluid. The lighting system 205 is a stroboscopic lighting system where light pulses are synchronized with the video capture. Preferably, the lighting system 205 is based on one or more LED diodes which light the flow 21 which circulates through the micromechanical cell 20 at regular flashes of light. In other words, the lighting system preferably comprises at least one LED emitter 205. More preferably, a plurality of LED diodes is used. In embodiments of the invention, between 3 and 6 LED diodes are used. When more than one LED is used, the plurality of LEDs may be disposed in serial configuration or in parallel configuration. The lighting system 205 is described in detail later in this text.

Between the lighting system 205 and the flow of fluid 21 (which circulates inside a pipe), a diffuser 204 may be placed for diffusing the amount of light emitted by the lighting system 205 in order to obtain a homogenous lighting over the entire area (amount of fluid) that is being inspected. In embodiments of the invention, the diffuser 204 is a window, understood as an element providing visual access to the fluid under inspection. The diffuser or diffuser window enables to light the area under inspection in a homogeneous manner. The diffuser or diffuser window 204 may be implemented as closing a hole made in the pipe through which the fluid 21 flows. The diffuser 204 is moreover made of a transparent material, such as a glass, for example a frosted glass, which allows light passing through it after diffusing it.

Opposite the lighting system 205, on the other side of the pipe through which the flow 21 circulates, the image capture system 201 is situated to capture the video sequence (a train of images) of the zone of interest in the passage of the fluid. This image capture is carried out with a defined spatial resolution and maintaining the general criteria of reduced size and low cost. In other words, the "defined spatial resolution" refers to the fact that the capture system 201 is capable of determining a defined minimum size of particle (even particles having a largest dimension of 1 µm (for example diameter of 1 µm) can be measured) taking into account the instant velocity of the fluid in which the particles are suspended. This is exemplified later with respect to FIG. 5.

The image capture system 201 is a camera implementing the Rolling Sutter with Global Start (RSGS) functionality. More preferably, it is a RSGS camera based on CMOS sensor or CMOS detector (the CMOS sensor is the camera component that receives the image). Therefore, a CMOS camera has a 2D array of photoreceptors manufactured with CMOS technology. For this reason, occasionally in this text the expression "CMOS sensor" or "CMOS detector" is used to refer to the image capture system 201. Alternatively, the image capture system 201 is a charge-coupled device camera (CCD camera) implementing the (RSGS) functionality. The images captured by this camera are processed in the processing means 2061, which analyses for each image whether there are bubbles and particles (and, in embodiments of the invention, counts them) and determines the size and shape of the detected objects (bubbles and particles). In other words, the processor extracts the image from the CMOS and processes it. To do this, it has an intermediate memory (not shown) for subsequent processing. In a possible embodiment, this intermediate memory is a DDR2 external memory.

Between the image capture system 201 and the flow of fluid 21 under inspection there may be a lens 202, preferably a macro lens, for transporting the image from the object to the camera 201. The lens allows objects to be focused in the light-reactive element and objects to be captured. The lens carries the light in focus to the light receiving area.

Between the lens 202 and the pipe that collects the flow of fluid 21 under inspection there may be an optical window 203 sealing a hole made in the pipe. This hole is opposite the hole described above (and covered by the diffuser 204). This second optical window 203 is also made of a transparent material that allows light to pass through it. The window 203 is a calibration window which comprises markings or patterns that allow it to be auto-calibrated, as explained in EP2980557A1.

The minimum size of objects that the system is capable of discriminating is of approximately 1 µm. The area to be captured in each image by the image capture system 201 must be such that it is capable of capturing objects of 1 µm (and of course, bigger ones) across a total capture area of several tens of mm². In a preferred embodiment, the area to be captured is of several mm². In one example, said area to be captured is of 100 mm². At the same time, the distance between the object (plane of passage of the fluid under inspection) and the image capture system 201 is desirably as minimum as possible and does not exceed approximately 40 mm, so that the system can be as compact and small as possible. The maximum depth of field (range in which the lens 202 is capable of providing a focused image) is marked by the width of the passage of the fluid through the micromechanical cell 20.

Figure 2:
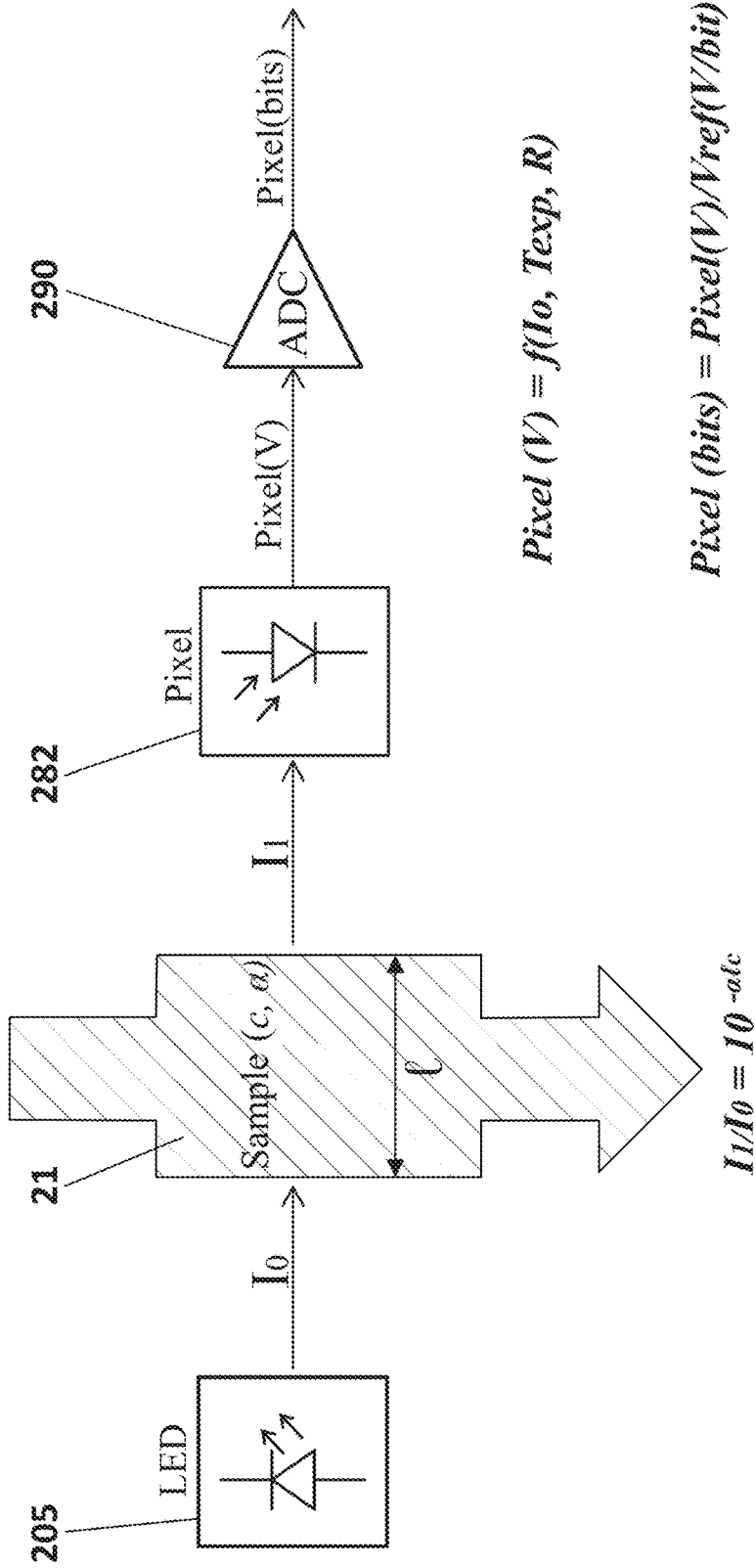
FIG. 2 represents the problem observed when applying RS in a system for inspecting a moving fluid.

FIG. 2 represents the problem observed when applying RSGS in a system as shown in FIG. 1. This problem relates to the received optical power at the image capture system 201. In order for the system 1 to perform correctly, there must be enough light travelling through the fluid under supervision, in such a way that an image having enough contrast is generated and captured. A person skilled in the art knows that the image processing is only possible with images of enough quality in terms of focusing contrast. FIG. 2 shows the amount of light Pixel(V) captured by each pixel 282 and converted into a digital voltage level Pixel(bits) by an analog-to-digital converter ADC 290 included adherent to the pixels within the CMOS sensor device. Pixel(bits) refers to the digital representation (in bits) of an analogue magnitude, such as the current or voltage (Pixel V) generated by each pixel when it receives light. Pixel(bits)=Pixel(V)/Vref (V/bit). Vref refers to the voltage reference of the CMOS in order to perform such digitalization of the received light. LED 205 emits light pulses (stroboscopic pulses) of duration $T_{on}$ (ms), having certain light intensity $I_O$ wherein $I_0$(lux)= $I_{pol}$ (A) ρ(lux/A), $I_{pol}$(A) being the polarization current and ρ(lux/A) being the LED efficiency. The light $I_1$ received by pixel 282 (this light $I_1$ is essential for achieving good contrast) depends on the intensity of the emitted light $I_O$, on the absorbance $10^{-\alpha lc}$ that takes place in the sample 21 under analysis (the absorbance is dependent on the chemical properties c, α of the fluid and on the width l of the pipe; for example, opaque fluids have much larger absorbance than transparent fluids), on the responsivity R of the photodiodes forming each pixel (responsivity refers to the efficiency of the photodiodes in converting light energy into volts) and on the selected exposure time $T_{exp}$ (time for which a pixel is accumulating incident light) which, in RSGS systems is determined (limited) by the pulse duration $T_{ON}$, as will be explained later. As can be observed, parameters of different nature have an impact on the performance of the system: constructional parameters of the LED and pixels (ρ, R); physical and chemical parameters (absorbance, dependent on the fluid under supervision); and design parameters, such as the LED polarization current $I_{pol}$, the exposure time $T_{exp}$ of the pixel (or its photodiodes) and the pulse duration $T_{ON}$. These last parameters are the only ones under designer's choice to adjust the power of the received light in order to analyze a sample of fluid with enough contrast towards a correct discrimination of objects (particles, bubbles) suspended in the fluid. The range of LED polarization current $I_{pol}$ permits to inspect a certain range of fluids, defined by their absorbance which, together with the pulse duration $T_{ON}$ (which limits the exposure time $T_{exp}$) determines the maximum velocity of the particles.

Figure 3:
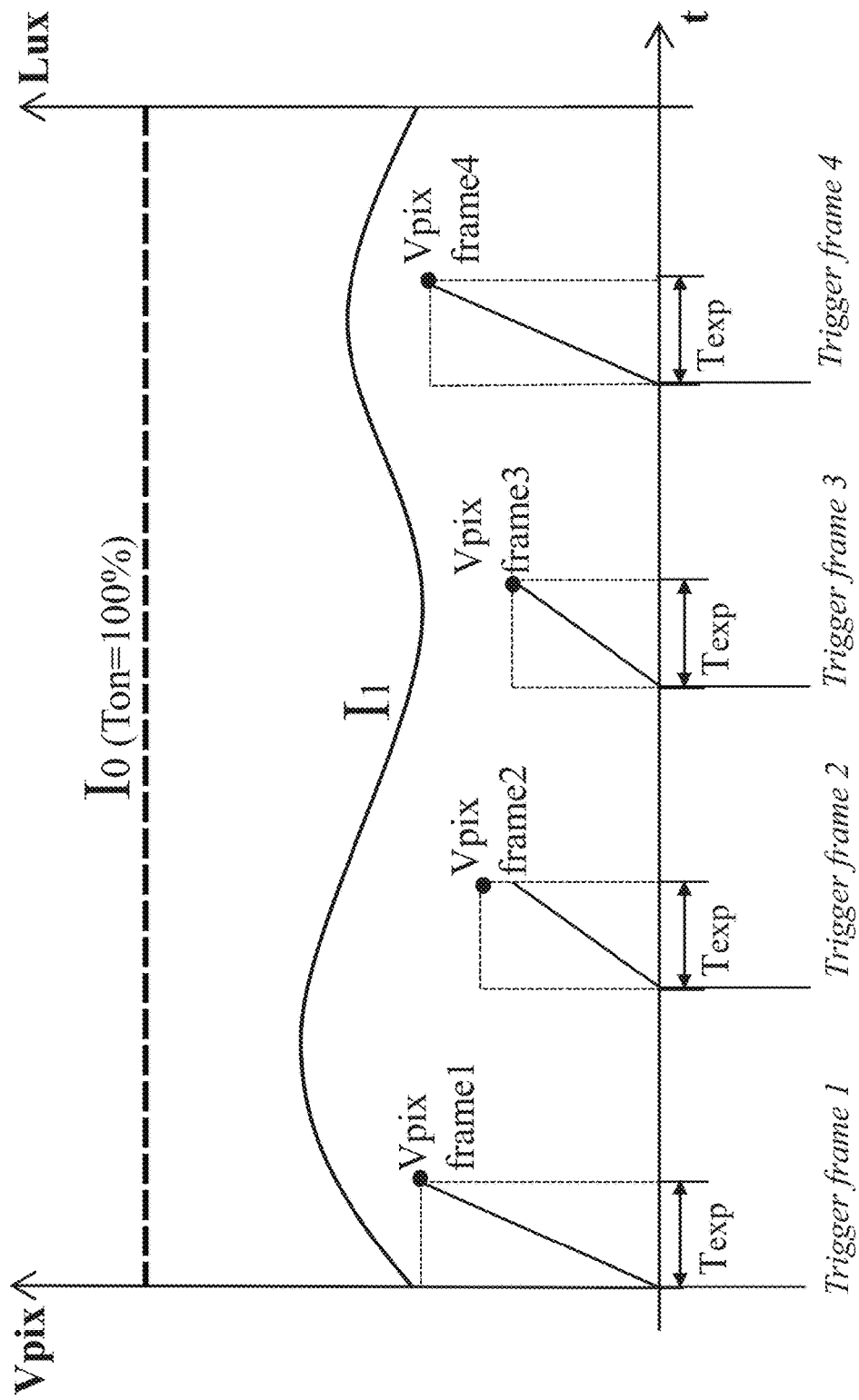
FIG. 3 represents the power received in a system for inspecting a moving fluid when applying conventional RS.

FIG. 3 represents a conventional system in which the lighting system continuously provides a flash light (flash always on or $T_{on}$=100%). Under these circumstances, the following equation describes the signal received by each pixel in each frame (a frame comprises a plurality of pixels forming a M×N matrix, being M~1900 pix and N~2600 pix), considering that the variations of $I_1$ within the time interval $T_{exp}$ are negligible (in FIG. 3, $I_1$ is represented as non-constant in order to express that the fluid under supervision may vary its absorbance as it is a flowing, non-static, sample):

$$Vpix(V) = I_1(lux) \times T_{exp}(sec) \times R\left(\frac{V}{lux \times sec}\right)$$

Figure 4:
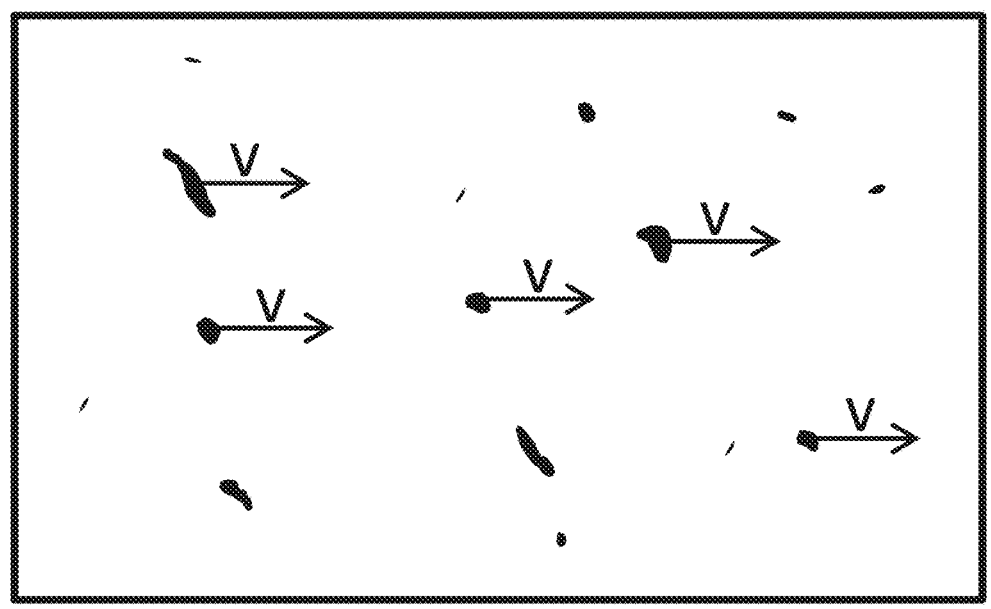
FIG. 4 shows the focusing area of a typical CMOS sensor, in which particles move at velocities varying between 3 and 22 m/s.

The duration of the lighting pulse of the stroboscopic lighting system 205 is defined by the expected velocity of the objects (particles) suspended in the fluid under supervision when they go through the focusing area. In other words, since the goal is to detect moving particles, the maximum pulse duration is given by the maximum particle velocity under observation. The lower the travelling velocity of the particles under examination is, the higher the duration of the lighting pulse may be. In contrast, the higher the travelling velocity of the particles under examination is, the lower the duration of the lighting pulse will have to be in order to avoid distortion. In a particular embodiment in which the supervision system 1 is applied to industrial machines, and more precisely to the lubricating oil they use, it has been observed that a typical working pressure may vary for example between 2 bar and 10 bar. In this case, the velocity of the objects (particles) suspended in the fluid (in this case, oil) varies between 3 m/s and 22 m/s, respectively. This means that it is expected that the samples under analysis travel following a laminar flow of velocities varying between 3 and 22 m/s. This means that the particles suspended in the fluid will also move at similar velocities (not considering turbulence effects, etc.). FIG. 4 shows the focusing area of a typical CMOS sensor, in which particles move at velocities varying between 3 and 22 m/s.

However, even if all particles are moving at the same velocity, the effect of the image capture distortion in Rolling Shutter does not affect large and small particles alike. Large particles, even with a small distortion, will be detectable by the vision algorithms (that are out of the scope of the present invention; see for example EP2980557A1) and there is no significant impact (actual particle size~object size detected). However, as the particle size is reduced, the effects of the distortion are more pronounced, impacting both on the size and in its apparent shape (for example, a circular particle will be seen as an ellipse due to the effect of distortion). What is more, in small particles, the distortion causes them to be non-perceptible.

Figure 5:
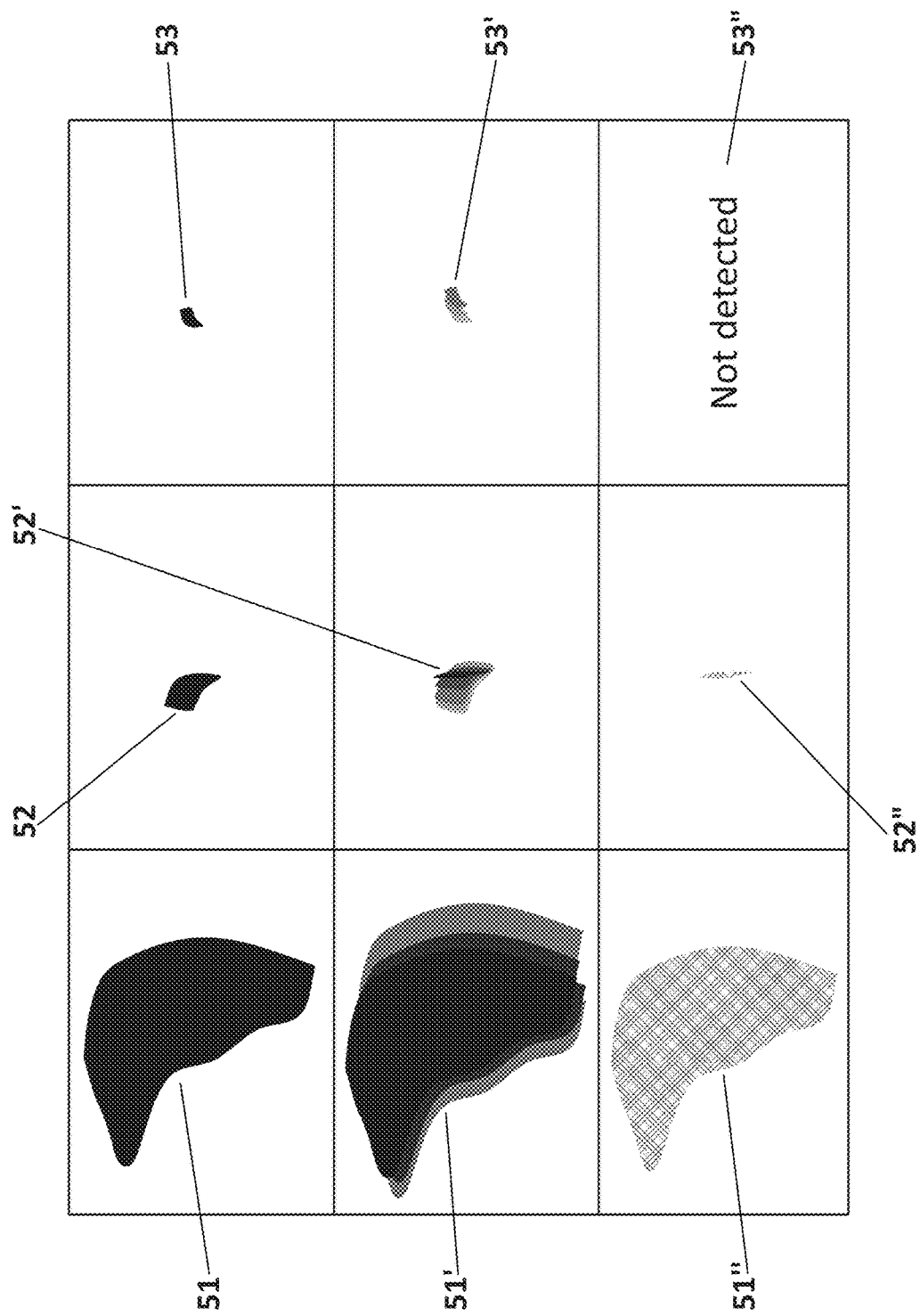
FIG. 5 shows a comparison of the performance of RS in moving fluids with respect to the size of the particles comprised in the moving fluid.

FIG. 5 shows a comparison of the performance of RSGS in moving fluids with respect to the size of the particles comprised in the moving fluid. First column refers to a big particle 51 (for example having a largest dimension larger than 14 μm), second column refers to a medium-size particle 52 (for example having a largest dimension between 6 and 14 μm) and third column refers to a small particle 53 (for example having a largest dimension varying between 1 and 6 μm). Second row shows how each particle 51 52 53 is captured with distortion 51' 52' 53'. Third row shows how the applied vision algorithms recognize each particle: the big particle is correctly recognized 51" (with minimum-negligible-impact), the medium-size particle is detected, but its size and shape is erroneously identified 52". Finally, the small particle is not detected at all 53".

Therefore, a criterion can be applied to determine from which percentage of distortion we have a fatal impact for detection. Defining for example that distortion will cause a bad detection if 50% of the area of the object is affected, the following table shows the maximum duration of the lighting pulse of the stroboscopic lighting system 205 for different object sizes (largest dimension) and speeds:

| Object size | 4 μm (small object) | 10 μm (medium object) | 20 μm (big object) |
|---|---|---|---|
| 50% distortion | 2 μm | 5 μm | 10 μm |
| Flowing velocity (m/s) | Maximum acceptable duration of lighting pulse | | |
| | 4 μm (small object) | 10 μm (medium object) | 20 μm (big object) |
| 1.5 | 1.3 μs | 3.3 μs | 6.6 μs |
| 3 | 600 ns | 1.6 μs | 3.33 μs |
| 11 | 180 ns | 450 ns | 900 ns |
| 22 | 90 ns | 230 ns | 450 ns |

This means that, depending on the target object size and on its expected velocity, the duration of the lighting pulse should vary between 80 ns and 10 μs approx.

Figure 6:
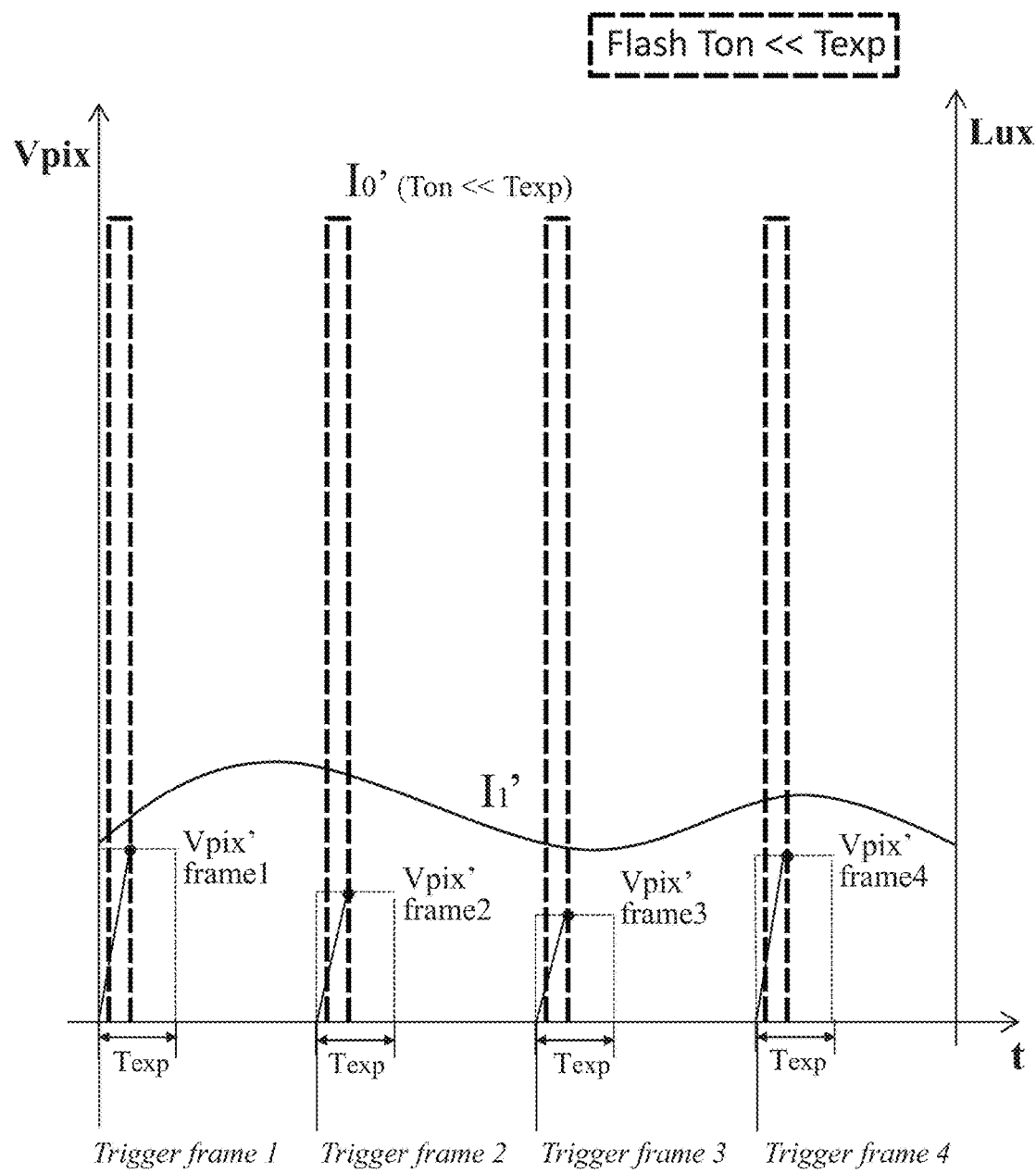
FIG. 6 represents the power received in a system for inspecting a moving fluid according to an embodiment of the invention, in which the duration of the flash light applied by the lighting system is much shorter than the exposure time of the pixels of the image capture system.

FIG. 6 represents a system in which the duration of the lighting pulse (flash on) $T_{ON}$ from the lighting system has been selected to be $\ll T_{exp}$. Then, the effective exposition time=$T_{ON}$. Under these circumstances, the following equation describes the signal received by each pixel in each frame (a frame comprises a plurality of pixels), considering that the variations of $I_1'$ within the time interval $T_{exp}$ are negligible:

$$Vpix'(V) = I_1'(lux) \times (T_{exp}(sec) \cap T_{Flashon}(sec)) \times R\left(\frac{V}{lux \times sec}\right) =$$
$$I_0'(lux) \times 10^{-A} \times T_{Flashon}(sec) \times R\left(\frac{V}{lux \times sec}\right)$$

Therefore, since the design goal is to maintain the signal generated by each pixel ($V_{PIX}$=$V_{PIX}$), that is to say, in spite of having pulses of short duration, the total light power must be similar to the one that would be obtained with a pulse always on (because high light power is required for acquiring images with good contrast), given certain values of absorbance (A) and pixel responsivity (R), the light intensity $I_0'$ emitted by the lighting system must be modulated. However, because $T_{ON} \ll T_{exp}$, in order to achieve that $V_{PIX}$=$V_{PIX}'$) the applied light power must be very high: $I_0' \gg I_0$.

Therefore, coming back to FIG. 1, in order to be able to inspect opaque fluids (worst case, since opaque fluids require more light power than transparent ones) having suspended objects having a largest dimension as small as 1 μm, flowing at high flow rates, the lighting system 205 must be capable of delivering very high power pulses for very short time duration. Besides, these pulses must be synchronized with the start instants of capture at image capture system 201. In the context of the present invention, the term "high" in "high flow rates" refers to flow rates varying between 1 and 40 m/s, that is to say, flow rates of up to 40 m/s. In the context of the present invention, the term "high" in "high power pulses" refers to power pulses varying between 20 mA and 20 A, preferably between 2 and 15 A. In the context of the present invention, the expression "very short" in "very short time duration" refers to time duration varying between 50 ns and 50 μs, preferably between 50 ns and 20 μs, more preferably between 50 ns and 10 μs, and still more preferably varying between 50 ns and 5 μs.

Figure 7:
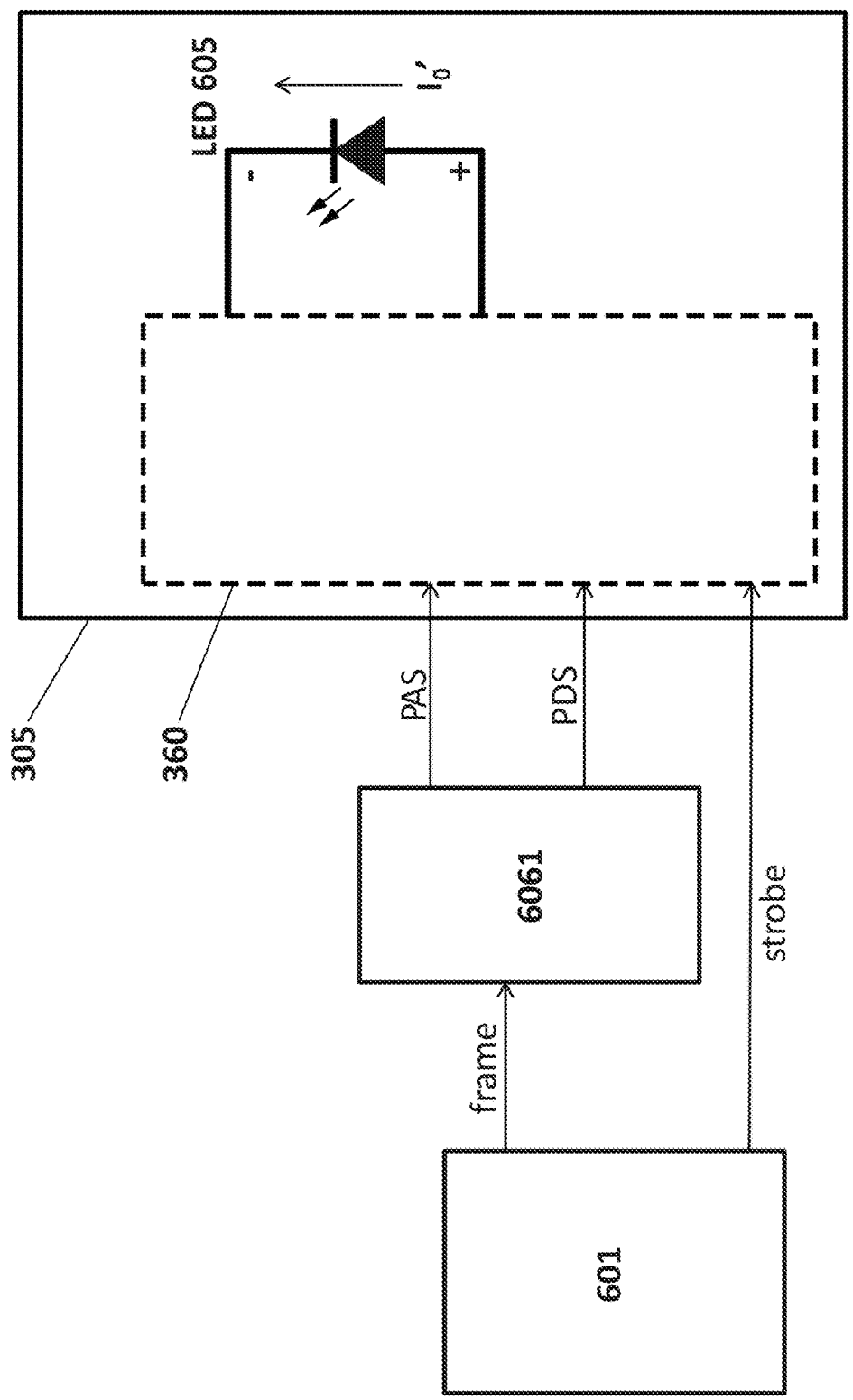
FIG. 7 shows in block diagram the image capturing system, processing means and lighting system of the monitoring system according to an embodiment of the invention.
Figure 8:
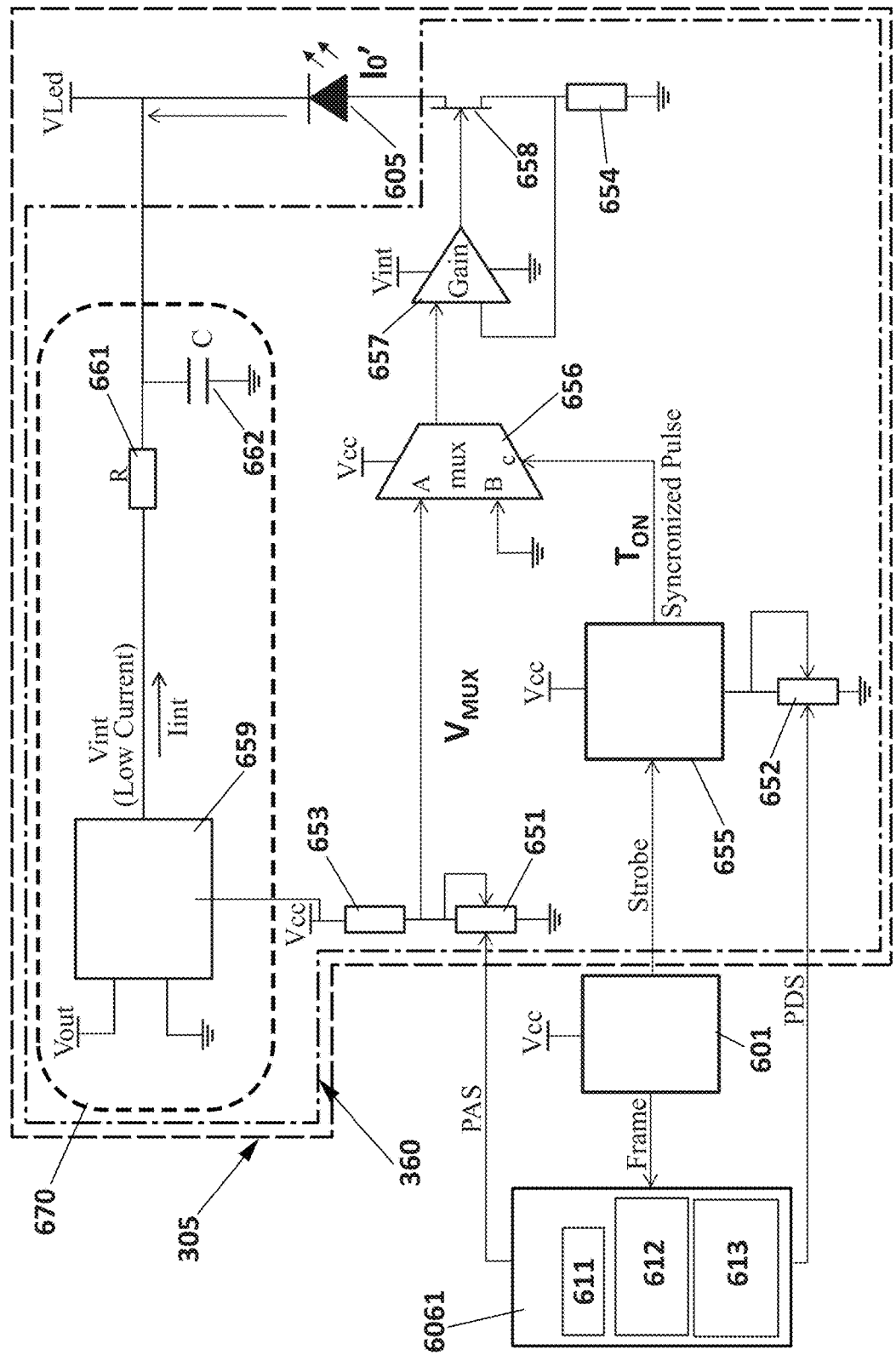
FIG. 8 shows a more detailed scheme of the lighting system of the monitoring system according to an embodiment of the invention.

This is achieved by a monitoring system 1 having an image capturing system 601 (201 in FIG. 1), processing means 6061 (2061 in FIG. 1) and lighting system 305 (205 in FIG. 1) as schematized in FIGS. 7 and 8. The lighting system 305 is configured for operating synchronized with an image capturing system configured in RSGS mode.

FIG. 7 shows in block diagram the image capturing system 601 (201 in FIG. 1), processing means 6061 (2061 in FIG. 1) and lighting system 305 for operating synchronized with the image capturing system 601 configured in RSGS mode, of the monitoring system 1. The lighting system 305 comprises at least one LED diode 605 and light driving means 360 for operating the at least one LED diode 605. FIG. 8 shows in detail the blocks of FIG. 7. In particular, the light driving means 360 for operating the at least one LED diode 605 is shown in more detail. The lighting system 305 is capable of detecting objects (such as particles and bubbles) of microscopic size, suspended in moving fluids potentially very opaque. With the lighting system 305 of the invention, particles having a dimension (i.e. diameter) larger than 1 μm are detected.

The lighting system 305 has one or more LED diodes 605 (also referred to as LED or LEDs) that may be disposed in serial or in parallel or in a mixed serial/parallel configuration. The current Io' travelling through the at least one LED 605 must be a high current and high voltage delivered at fast pulses. In a particular embodiment, each LED needs current $I_O'$=6 A and voltage=5 V. In an exemplary implementation, in which 6 LEDs are disposed in serial configuration, the required current and voltage is: $I_O'$=6 A, V=30 V. In another exemplary implementation, in which 6 LEDs are disposed in parallel configuration, the required current and voltage is: $I_O'$=36 A, V=5 V. The value of the amplitude of this current $I_O'$ and the duration of the current pulses delivered by the at least one LED 605 is controlled by processing means 6061 from the frames provided by the image capture system 601.

Each of these frames comprises the information captured by at least some of the pixels comprised in the image capture system 601 (preferably CMOS camera). The information captured by each pixel is a voltage (Vpix), then converted into digital value (bits), as explained with reference to FIG. 2. The Vpix resolution is given by the number of bits of the CMOS sensor (normally 8, 10 or 12 bits), in such a way that the information kept by a pixel can be discriminated into $2^n$ steps within the range 0-Vref, n being the number of bits used by each pixel (in other words, the pixel resolution). In a particular embodiment, each frame comprises the voltage captured by all of the pixels comprised in the image capture system 601. Each pixel carries a digital value representing the received light intensity.

Figure 9:
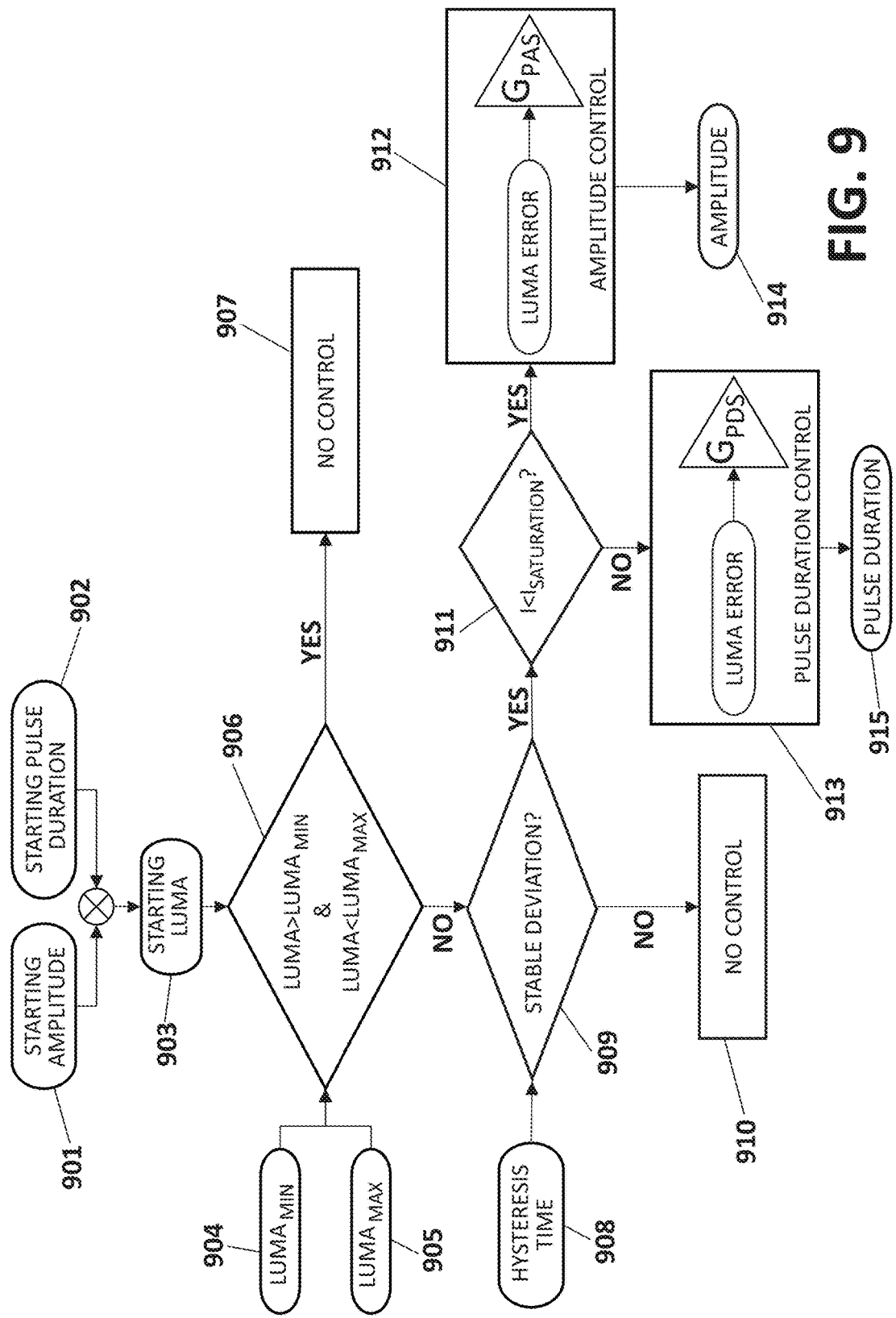
FIG. 9 shows a flow chart of an algorithm for calculating a pulse amplitude setpoint and a pulse duration setpoint from the frame light intensity according to an embodiment of the invention.

Referring now to FIG. 8, processing means 6061 has means 611 for reading each frame, means 612 for calculating, from each read frame, a frame light intensity $I_{frame}$ and means 613 for calculating a pulse amplitude setpoint (PAS) and pulse duration setpoint (PDS) from said frame light intensity $I_{frame}$. These setpoints PAS, PDS are instructions to be sent to respective digital potentiometers 651 652 in order to respectively establish the current and pulse duration. An algorithm calculates setpoints PAS, PDS from the frame light intensity (intensity of each frame) $I_{frame}$. In embodiments of the invention, the algorithm is a proportional-integral (PI) controller that prioritizes current increases over pulse duration in order to make it compatible with higher flows. In other embodiments, the setpoints PAS, PDS are calculated from the intensity of each frame $I_{frame}$ and from the contrast of each frame. FIG. 9 shows a flow chart of the algorithm for calculating setpoints PAS, PDS according to an embodiment of the invention. The algorithm is described next.

The frame light intensity $I_{frame}$ is preferably calculated as follows:

$$I_{frame}=(\Sigma Vpix)/NumPix$$

wherein Vpix is the voltage captured by each pixel in the image capture system 601 and NumPix is the amount of pixels in the image capture system 601.

As mentioned, block 613 comprises an algorithm for calculating a pulse amplitude setpoint (PAS) and pulse duration setpoint (PDS) from every new frame light intensity $I_{frame}$. The goal of this block 613 is to determine the new values of PAS and PDS in order to obtain a value of frame light intensity $I_{frame}$ (referred to as LUMA in FIG. 9) within lower and upper limits $I_{frame\_MIN}$, $I_{frame\_MAX}$ (respectively referred to as $LUMA_{MIN}$, $LUMA_{MAX}$ as in FIG. 9) defined by design. The starting points are current PAS 901 and PDS 902, together with the frame light intensity $I_{frame}$ (or LUMA) generated with the initial configuration of PAS, PDS. The goal of this control algorithm is to reach a value of $I_{frame}$, such that $I_{frame\_MIN}<I_{frame}<I_{frame\_MAX}$ ($LUMA_{MIN}<LUMA<LUMA_{MAX}$) while prioritizing raising the pulse amplitude (PAS) rather than raising the pulse duration (PDS), because it has been observed that this prioritizing scheme optimizes the compatibility with higher particle velocities. It is remarked that PAS and PDS values respectively control the values of potentiometers 651 652 respectively controlling the current $I_O'$ (Amperes) and the pulse duration $T_{ON}$ (μs). In a particular embodiment, potentiometers 651 652 are digital potentiometers. For example, they may be 8-bits potentiometers. This means that PAS and PDS are values varying between 0 and 255. In turn, the frame intensity is also represented as a certain level. In a particular embodiment, in which the camera is a CMOS camera of, for example, 8 bits, a level varying between 0 and 255 represents a mean luminance of all the pixels of the image captured by the CMOS. Therefore, the threshold intensity values $LUMA_{MIN}$, $LUMA_{MAX}$ correspond to certain luminance levels (varying for example between 0 and 255). A non-limiting typical design value of LUMA for a certain frame is 150. So, turning back to FIG. 9, the starting points of PAS 901 and PDS 902 provide a starting point of luminance (or LUMA) 903.

Then, considering threshold design parameters $LUMA_{MIN}$ 904 and $LUMA_{MAX}$ 905, the algorithm checks (block 906) whether the current luminance 903 is within the established threshold: current LUMA>$LUMA_{MIN}$ and current LUMA<$LUMA_{MAX}$. Non-limiting exemplary values of minimum luma $LUMA_{MIN}$ 904 and maximum luma $LUMA_{MAX}$ 905 are $LUMA_{MIN}$=130 and $LUMA_{MAX}$=170 (for levels varying between 0 and 255). If $LUMA_{MIN}$<current LUMA<$LUMA_{MAX}$, then (block 907) no control is required (end of the algorithm). If, on the contrary, the former condition is not fulfilled, in block (909) it is checked the time duration of the deviation with respect to the established range ($LUMA_{MIN}$, $LUMA_{MAX}$). In other words, it is checked whether or not the deviation is stable in time, that is to say, how many consecutive frames have luminance out of ($LUMA_{MIN}$, $LUMA_{MAX}$). This hysteresis time 908 is also a design parameter. A non-limiting example of hysteresis time may be 5 seconds. So, if the current LUMA is out of the design range for a time duration shorter than the defined hysteresis time 908, no control is applied (block 910) and the algorithm is ended. If, on the contrary, the current LUMA is out of the design range for a time duration larger than the defined hysteresis time 908, a control must be applied.

Then, it is first checked (block 911) whether or not the current pulse amplitude setpoint PAS corresponds to a maximum value of intensity (saturation current). In a non-limiting example, the saturation current may be 6 A. In other words, it is checked (block 911) whether current PAS=$PAS_{MAX}$. If PAS<$PAS_{MAX}$ (that is to say, current I<$I_{saturation}$), then (block 912) the following calculation is performed: new_PAS=($I_{frame}$−$I_{frame\_setpoint}$)×Gain_PAS, wherein $I_{frame}$ the actual current (LUMA) and $I_{frame\_setpoint}$ (also referred to is as $LUMA_{setpoint}$) is the frame intensity (LUMA) to be reached. For example, if $I_{frame\_setpoint}$=160 and $I_{frame}$=120, the control algorithm will try to obtain $I_{frame}$=160 for the following frames by applying a gain. In a particular example, $LUMA_{setpoint}$=($LUMA_{MAX}$+$LUMA_{MIN}$)/2. In block 912, the applied gain is referred to as $G_{PAS}$. The value of new_PAS (block 914) is used to update potentiometer 651. In other words, the resistance value of potentiometer 651 is adjusted to the value that enables the pulse amplitude to be as required.

If, on the contrary, PAS=$PAS_{MAX}$ (that is to say, current I=$I_{saturation}$), then the pulse amplitude cannot be raised anymore. Therefore, the only parameter to be adjusted in order to control $I_{frame}$ (that is, LUMA) is the pulse duration. In order to do so, in block 913 the following calculation is performed: new_PDS=($I_{frame}$−$I_{frame\_setpoint}$)×Gain_PDS. In block 913, the applied gain is referred to as $G_{PDS}$. The value of new_PDS (block 915) is used to update potentiometer 652. In other words, the resistance value of potentiometer 652 is adjusted to the value that enables the pulse duration to be as required.

Figure 10:
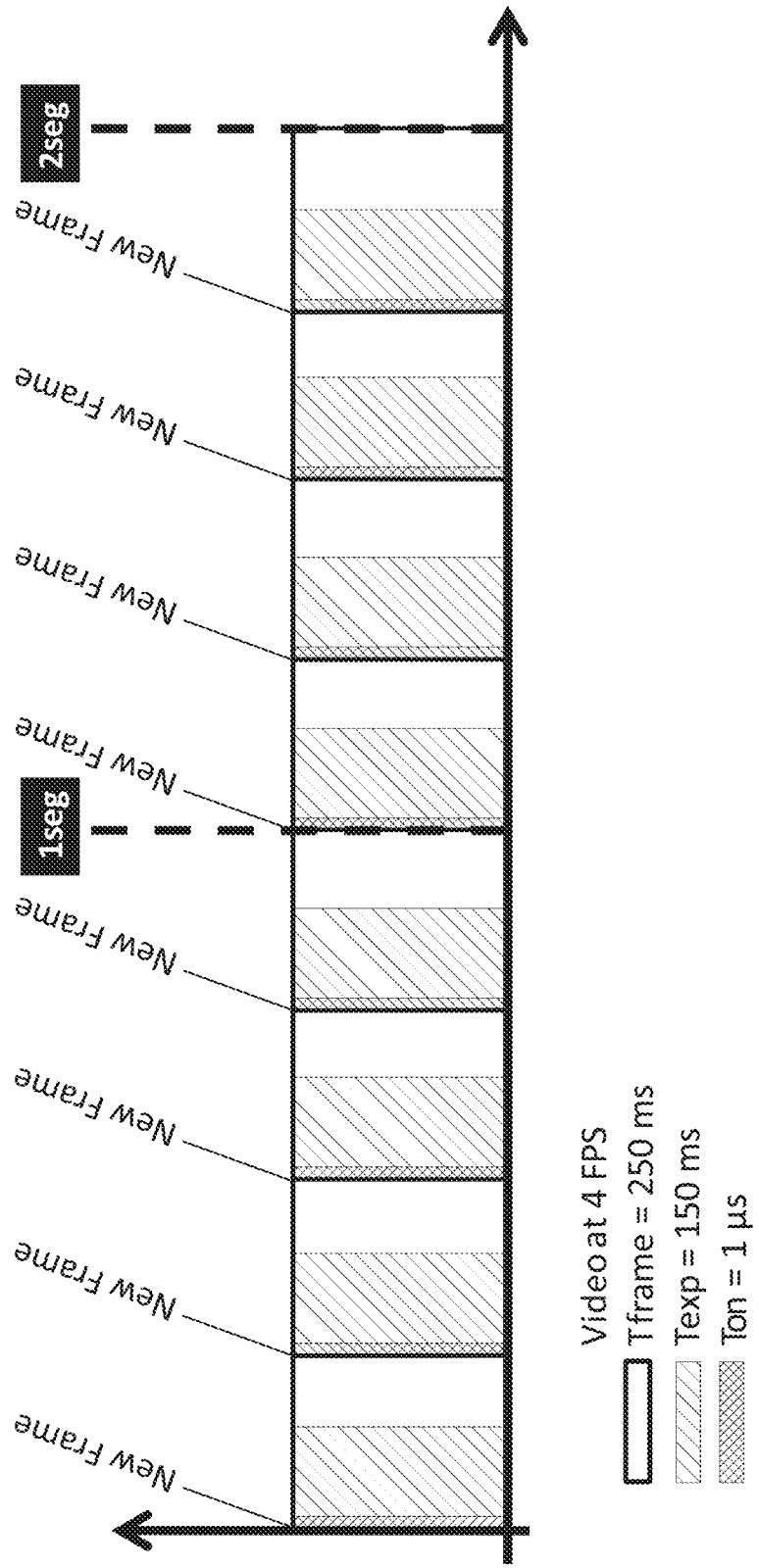
FIG. 10 shows an example of exposure time $T_{EXP}$, $T_{frame}$ and $T_{ON}$ according to an embodiment of the invention.

As explained in relation to the algorithm illustrated in FIG. 9, the PDS is used for controlling the pulse duration $T_{ON}$ of a pulse signal, that is to say, the time for which the lighting system 305, or more precisely, the at least one LED 605, is on (emitting power). The pulse signal (and pulse duration $T_{ON}$) is created at a pulse generator 655. In a particular embodiment, the pulse generator 655 is implemented with a single retriggerable monostable, such as a single retriggerable monostable chip, provided for example by Texas Instruments. The pulse generator 655 provides a pulse signal having period $T_{frame}$ and having pulses of duration $T_{ON}$, $T_{ON}$<<$T_{frame}$. In order to define the pulse duration $T_{ON}$, the pulse generator 655 uses the PDS (that basically configures an RC net of the retriggerable monostable, which is a common way of configuring chips of this kind). The pulse generator 655 also uses a flash signal (also referred to as strobe signal) provided by the image capture system 601. The strobe signal triggers the start of the flash duration, and it is a parameter of the image capture system, in particular, of the CMOS camera, which provides a strobe signal having certain frequency correlated with the Frames per Second ($T_{frame}$) configuration. Therefore, the strobe signal is used as a trigger signal. This strobe signal provided by the image capture system 601 is used by the pulse generator 655 for synchronizing the generated signal (having period $T_{frame}$ and having pulses of duration $T_{ON}$) with the strobe signal of the image capture system 601. The PDS signal is fed into the digital potentiometer 652. Potentiometer 652 controls, by means of its variable resistance R (adjusted from PDS) in a RC network (capacitor not explicitly shown in FIG. 8), the duration of the short pulses (duration $T_{ON}$) generated by pulse generator 655. In other words, potentiometer 652 fixes a value of the RC network that defines the operation of the pulse. Therefore, the pulse generator 655 calculates the pulse duration $T_{ON}$ (the very short time duration of the high power pulses emitted by the at least one LED 605) from the PDS. The strobe signal is used for triggering each pulse of duration $T_{ON}$. In other words, the strobe signal permits to work in synchronization between lighting system and image capture system. This way, the light pulses emitted by the at least one LED 605 are synchronized with the strobe signal of the image capture system 601 (the light pulses emitted by the at least one LED 605 are triggered at the time instant at which each pixel starts to capture a frame). As a matter of example, let's consider an image capture system 601 whose pixels have exposure time $T_{EXP}$=150 ms and video is captured at 4 FPS (frames per second, that is to say, $T_{frame}$=250 ms). This is exemplified in FIG. 10. If for example $T_{ON}$=1 µs, with every new frame (that is to say, every 250 ms, since $T_{frame}$ is the time period between two consecutive captured image frames) a new LED pulse is triggered. This triggering of each pulse of duration $T_{ON}$=1 µs is synchronized with the starting of each exposure time $T_{EXP}$=150 ms.

The pulse duration $T_{ON}$ is directed to multiplexor 656 which provides at its output a reference voltage of duration the pulse duration $T_{ON}$, and a substantially null voltage when there is no pulse duration $T_{ON}$. The duration of the null voltage depends of the frames per second (FPS) at which the camera works. For example, if it works at 20 FPS, then the duration of the null voltage is 50 ms. The minimum duration of the null voltage is approximately 1 ms. In other words, multiplexor 656 provides a reference voltage $V_{MUX}$ for the time the at least one LED 605 must be on and provides a null voltage for the time the at least one LED 605 must be off. This reference voltage $V_{MUX}$ is then converted into the polarization current of the at least one LED 605. How this reference voltage $V_{MUX}$ is calculated is explained next.

Turning back to processing means 6061, processing means 6061 delivers a PAS to a potentiometer 651. As explained in relation to the algorithm illustrated in FIG. 9, PAS value defines the value taken by variable potentiometer 651, in such a way that $V_{MUX}$=(resistance of potentiometer 651)/(resistance of potentiometer 651+resistance of resistor 653)×Vcc. So, the PAS is used for calculating a reference voltage $V_{MUX}$, in turn used for calculating current Io' travelling through the at least one LED 605. This is done at multiplexor 656, wherein either $V_{MUX}$ or a null voltage is provided to amplifying means 657, which provides flash gain. As explained above, $V_{MUX}$ is provided for the time duration $T_{ON}$ of the pulse generated by pulse generator 655, while a null voltage is provided for the time duration at which the pulse generated by pulse generator 655 has null amplitude. This time duration can be referred to as $T_{OFF}$. Processing means 6061 configures the frames per second (FPS) at which the camera (CMOS) works. These FPS in turn fixes $T_{OFF}$=$T_{frame}$−$T_{ON}$. At the output of amplifying means 657 a driving voltage is applied to the mosfet transistor circuit 658, 654, which drives finally the high current Io' for the one or more LEDs 605. This high current Io' can be switched on and off very fast, allowing the generation of clean pulses. In a preferred embodiment, the on & off switching times of high current Io' are less than 10% of the time duration $T_{ON}$.

So far, a circuit has been described, capable of generating a current Io' delivered at pulses of duration $T_{ON}$ (for example 4 µs or less) and having high amplitude (for example 10 A) and $T_{OFF}$=$T_{frame}$−$T_{ON}$, of for example 20 ms (depending on the FPS at which the camera works). However, in order for the lighting system 205, 305 to correctly operate in RSGS mode, it is required that the very high power pulses maintain their amplitude exactly for the time duration $T_{ON}$ (pulses as square as possible), as represented in FIG. 6. In other words, Io' must switch from several Amperes to 0 Amperes immediately (preferably in less than 10% of the time duration $T_{ON}$) and the other way around. In order to fulfil such strict requirement, the lighting system 305 comprises a loading system 670 that makes the lighting system 305 independent from the power supply unit and that permits the lighting system 305 to work with a very low current power source (for example, 100 mA or even less). Loading system 670 stores energy in such a way that current Io' is available very quickly for driving the one or more LEDs 605. Therefore, system 670 is an energy storage means capable of transferring current very quickly. Because $T_{OFF} \gg T_{ON}$, $T_{OFF}$ is used for loading a capacitor, thus having the energy required for providing current Io' ready to be used. As one skilled in the art is aware of, the energy stored by a capacitor is given by $E=\frac{1}{2}*C*V^2$ wherein $V=V_{Led}$.

System 670 comprises a switched-mode power supply 659 which, from an external common DC power supply source $V_{out}$ provided by the industrial system in which the monitoring or inspection system 1 (FIG. 1) is integrated, generates a low current $I_{int}$ and voltage $V_{int}$ (voltage $V_{int}$ at the output of switched-mode power supply 659). A typical voltage $V_{out}$ provided by the industrial system is, for example, 24 V. Alternative typical values of $V_{out}$ are 5 V and 12 V. In other words, voltage $V_{int}$ is an intermediate voltage generated in order to enable the "low" loading of capacitor 662. In an exemplary embodiment, $V_{int}$ varies between 30 and 40 V. $V_{int}$ may vary depending on the configuration of the LED diodes 605 (serial or parallel configuration). This means that, although the lighting system 305 needs current Io' (for example, 10 A), a switched-mode power supply 659 may only provide a low current $I_{int}$. This low current $I_{int}$ is limited by the resistor 661 and sets the charging speed of the capacitor 662. In other words, resistor 661 regulates current $I_{int}$ because $V_{int}$ is normally fixed (design value). In embodiments of the invention, low current $I_{int}$ varies between 1 mA and 50 mA. The higher is current $I_{int}$, the quicker the capacitor 662 will be loaded. There may be one or more capacitors 662. In other words, capacitor 662 works as a pulse energy storage means, while resistor 661 regulates the charging speed of the pulse energy storage means 662 ($I_{int}=V_{int}$/resistance value of 661). The RC circuit (661, 662) is configured in such a way that capacitor 662 becomes fully charged in a time τ smaller than $T_{EXP}$ ($T_{EXP}$ depends on the image capture system). So, when capacitor 662 is fully charged, it stores enough energy to commute Io' current keeping $V_{LED}$ stable. In other words, $V_{Led}$ works as the source that provides the current Io' imposed by processing means 6061 (through PAS). $V_{Led}$ is $V_{int}$ but with capacity of providing a high current through the energy stored in the capacitors 662. Finally, Vcc is the voltage for feeding the remaining electronic circuits (a typical value of Vcc is 3.3 V).

Figure 11:
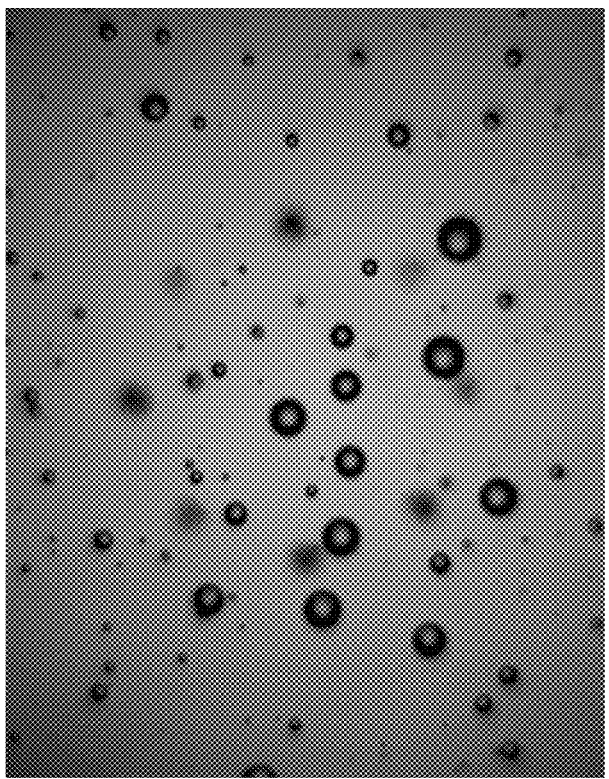
FIG. 11 shows a comparison of performance of a system according to the invention (right) versus a conventional system based on Rolling Shutter (left).
Figure 11:
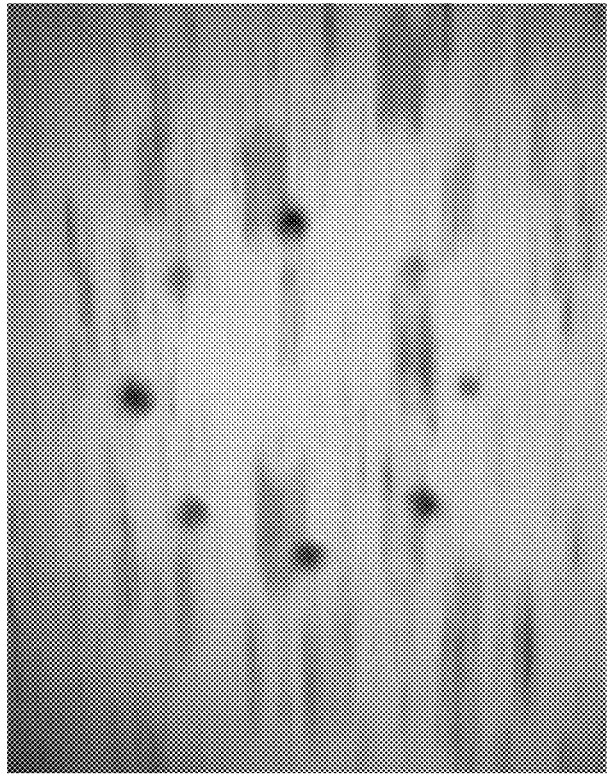

FIG. 11 shows a comparison of performance of a system according to the invention (right) versus a conventional system based on Rolling Shutter (left). In both cases the frame rate=42 fps ($T_{frame}$=1/42=23 ms) and the exposure time $T_{EXP}=T_{frame}$=23 ms. Using a conventional system (left), having flash always on ($T_{ON}$=23 ms (100%), the objects (bubbles) captured by the image capture system and processed at processing means are distorted. In other words, with an exposure time (that is to say, a flash time on) of 23 ms, moving objects appear distorted. In this case, the brightness (or contrast) of the image is determined by the 23 ms of exposure time ($T_{EXP}$). In the conventional system (left), Io'=200 mA. On the contrary, using a system according to the invention (right), having flash duration ($T_{ON}$)=4 μs (that is to say, in the order of 0.01% of $T_{frame}$), the objects (bubbles) captured by the image capture system and processed at processing means are not distorted. In this case (right), Io'=10 A. In this case, the effective exposure time is defined by the duration of the 4 μs Flash ($T_{ON}$), in spite of the exposure time ($T_{EXP}$) of the CMOS being 23 ms, allowing moving objects to be much clearer. What is more, the brightness of the image is also determined by the flash pulse because the flash duration ($T_{ON}$) and its power (Io') determine the amount of light received by the CMOS and therefore the brightness of the image. It is observed in this case that it has been necessary to amplify 50 times the illumination power (×50) (from 200 mA to 10 A) in order to obtain a contrast similar to the one on the left. However, in terms of LED life, it is much better to operate with short pulses of higher current than with 100% on with lower current, due to overheating occurring with the LED always on.

In sum, detection of moving objects having a largest dimension as small as 1 μm at flow rates of up to 40 m/s in opaque fluids and determination of their size and shape has been achieved by the system of the invention, provided that the image capture system receives enough power ($\propto T_{ON}$ and Io') for the fluid images and the objects suspended thereon to have enough contrast for its correct discrimination, and that the flash duration (duration of light pulses) is very short in order to obtain clear capture of the objects suspended in the fluid. This is achieved by a lighting system delivering very high power pulses (varying between 20 mA and 20 A) for very short time instants (varying between 50 ns and 50 μs). The microscopic objects shown in the images captured by the image capture system 601 substantially have the shape of the original microscopic objects located in the flowing fluid. This permits the later detection of their real size and identification of actual shape of the original microscopic objects suspended in the flowing fluid by means of techniques which are out of the scope of the present invention.

Throughout this document, the word "comprises" and variants thereof (such as "comprising", etc.) must not be interpreted as having an exclusive meaning, in other words, they do not exclude the possibility of what is being described incorporating other elements, steps, etc.

At the same time, the invention is not limited to the specific embodiments described herein and also extends, for example, to variants that may be embodied by an average person skilled in the art (for example, with regard to the choice of materials, dimensions, components, configuration, etc.), within the scope of what is inferred from the claims.

What is claimed is:

1. A system for detecting microscopic objects located in a flowing fluid, the system comprising:
    a lighting system comprising at least one LED diode and configured to supply light to the flowing fluid;
    an image capture system situated on the opposite side of the flowing fluid in respect of the lighting system, said image capture system being configured to capture a sequence of images of the flowing fluid, said image capture system comprising a camera in turn comprising a plurality of pixels;
    processing means configured to process said sequence of images and to determine the presence of microscopic objects within said flowing fluid and the shape of the microscopic objects,
    the system being characterized in that said lighting system is configured to supply high power light pulses having amplitude Io' and very short time duration $T_{ON}$, the time instant at which said pulses are triggered being synchronized with the time instants at which pixels in the image capture system start to capture an image frame, wherein said processing means is configured to control said amplitude Io' and time duration $T_{ON}$ of the light pulses supplied by the lighting system from said images captured by said image capture system, said control of amplitude Io' and time duration $T_{ON}$ being done by means for calculating, from the light intensity of each captured image frame, a pulse amplitude setpoint and a pulse duration setpoint for adjusting respective potentiometers configured to respectively fix the amplitude Io' and pulse duration $T_{ON}$ of the light pulses supplied by the lighting system, said means for calculating the pulse amplitude setpoint and the pulse duration setpoint being configured to execute an algorithm that prioritizes amplitude rises over pulse duration rises, said lighting system further comprising an energy loading system configured to make the amplitude requirement and response time of the lighting system independent from a power supply unit of the system.

2. The system of claim 1, wherein said image capture system is configured to provide said processing means with an image frame (Frame) captured every $T_{frame}$ seconds, $T_{frame}$ being greater than or equal to $T_{EXP}$, wherein $T_{EXP}$ is the exposure time of the pixels comprised in said image capture system.

3. The system of claim 1, wherein said lighting system comprises a pulse generator for generating from said pulse duration setpoint and from a strobe signal provided by said image capture system, a pulsed signal having period $T_{frame}$ and having pulses of duration $T_{ON}$, $T_{ON} \ll T_{EXP} \leq T_{frame}$, said duration $T_{ON}$ being obtained from said pulse duration setpoint and said strobe signal being used for synchronizing the pulses of duration $T_{ON}$ with the time instant at which the pixels in the image capture system start to capture an image frame.

4. The system of claim 3, wherein the pulse generator is implemented with a single retriggerable monostable forming, together with the potentiometer adjustable by the pulse duration setpoint, an RC network configured to fix said pulse duration $T_{ON}$.

5. The system of claim 1, wherein said lighting system further comprises a multiplexor configured to provide a reference voltage of duration $T_{ON}$, and a substantially null voltage of duration $T_{frame} - T_{ON}$, wherein said reference voltage $V_{MUX}$ is calculated from said pulse amplitude setpoint obtained at said processing means, said reference voltage being used for obtaining a polarization current of said at least one LED.

6. The system of claim 1, wherein said energy loading system comprises a switched-mode power supply configured to provide a voltage and a low current from an external DC power supply source; and an RC network comprising at least one capacitor and a resistor, wherein said at least one capacitor works as a pulse energy storage means and said resistor regulates the charging speed of the pulse energy storage means, said RC network being configured for the at least one capacitor to become fully charged in a time duration $T_{frame} - T_{ON}$, wherein $T_{frame}$ is the time period between two consecutive image frames captured by the image capture system, the switched-mode power supply thus providing a voltage in turn enabling to provide said at least one LED with said current Io'.

7. The system of claim 1, further comprising a diffuser situated between the lighting system and the flow of fluid, configured to provide homogeneous lighting to the area to be illuminated.

8. The system of claim 7, wherein said diffuser is situated closing off and sealing a hole made in the pipe through which the fluid flows.

9. The system of claim 1, further comprising a lens situated between the image capture system and the flow of fluid, configured to focus the captured images.

10. The system of claim 9, further comprising a calibration window situated between the lens and the flow of fluid.

11. The system of claim 1, wherein said processing means is configured to determine the presence and shape of objects having a largest dimension smaller than 20 μm.

12. The system of claim 1, wherein the light pulses supplied by the lighting system have amplitude Io' varying between 20 mA and 20 A and time duration $T_{ON}$ varying between 50 ns and 50 μs.

13. A method for detecting microscopic objects located in a flowing fluid, comprising:
supplying light emitted by at least one LED to a flowing fluid having microscopic objects suspended thereon;
capturing a sequence of images of the flowing fluid by means of an image capture system comprising a plurality of pixels;
processing said sequence of images and determining the presence of microscopic objects within said flowing fluid and the shape thereof,
the method being characterized by:
at said image capture system, capturing an image frame every $T_{frame}$ seconds, $T_{frame}$ being higher than or equal to $T_{EXP}$, wherein $T_{EXP}$ is the exposure time of said pixels comprised in said image capture system;
providing a strobe signal from said image capture system;
for each frame, calculating a pulse amplitude setpoint and a pulse duration setpoint from the intensity of each frame by executing an algorithm that prioritizes rises in the pulse amplitude rather than rises in the pulse duration;
at a pulse generator, receiving said pulse duration setpoint and generating from said pulse duration setpoint and from said strobe signal a pulsed signal having period $T_{frame}$ and having pulses of duration $T_{ON}$, $T_{ON} \ll T_{frame}$, said duration $T_{ON}$ being obtained from said pulse duration setpoint and said strobe signal being used for synchronizing the pulses of duration $T_{ON}$ with the time instant at which the pixels in the image capture system start to capture an image;
calculating a reference voltage of duration $T_{ON}$ from said pulse amplitude setpoint, said reference voltage being used for obtaining a polarization current of said at least one LED;
providing a voltage enabling to provide a current Io' to said at least one LED at pulses of duration $T_{ON}$, said voltage being provided by a an RC network comprising at least one capacitor and a resistor, wherein said at least one capacitor works as a pulse energy storage means and said resistor regulates the charging speed of the a pulse energy storage means, said RC network being configured for the at least one capacitor to become fully charged in a time duration $T_{frame} - T_{ON}$, wherein $T_{frame}$ is the time period between two consecutive image frames captured by the image capture system.

14. The method of claim 13, wherein said stage of, for each frame, calculating a pulse amplitude setpoint and a pulse duration setpoint from the intensity of each frame, is done as follows:

from current PAS, PDS and luminance generated with said PAS and PDS, checking whether the current luminance is within a design range $LUMA_{MIN}$<current $LUMA<LUMA_{MAX}$;

if $LUMA_{MIN}$<current $LUMA<LUMA_{MAX}$, then no control is required;

otherwise, it is checked whether the time duration of the deviation with respect to the established range is larger than a design hysteresis time and if the current luminance is out of the design range for a time duration shorter than the defined hysteresis time, then no control is required;

otherwise, it is checked whether or not the current pulse amplitude setpoint PAS corresponds to a maximum value of intensity and, if not, then (912) the following calculation is performed: new_PAS=$(I_{frame}-I_{frame\_setpoint})\times$Gain_PAS, the new_PAS value being used to update said potentiometer;

if the current pulse amplitude setpoint PAS corresponds to a maximum value of intensity the pulse duration is adjusted as follows: new_PDS=$(I_{frame}-I_{frame\_setpoint})\times$Gain_PDS, the value of new_PDS being used to update said potentiometer.

15. A computer program comprising computer program code means adapted to perform the steps of the method according to claim 13 when said program is run on a computer, a digital signal processor, a field-programmable gate array, an application-specific integrated circuit, a microprocessor, a micro-controller, or any other form of programmable hardware.

16. A method for detecting microscopic objects located in a flowing fluid, comprising:

supplying light emitted by at least one LED to a flowing fluid having microscopic objects suspended thereon;

capturing a sequence of images of the flowing fluid by means of an image capture system comprising a plurality of pixels;

processing said sequence of images and determining the presence of microscopic objects within said flowing fluid and the shape thereof, the method being characterized by:

at said image capture system, capturing an image frame every $T_{frame}$ seconds, $T_{frame}$ being higher than or equal to $T_{EXP}$, wherein $T_{EXP}$ is the exposure time of said pixels comprised in said image capture system;

providing a strobe signal from said image capture system;

for each frame, calculating a pulse amplitude setpoint and a pulse duration setpoint from the intensity of each frame by executing an algorithm that prioritizes rises in the pulse amplitude rather than rises in the pulse duration, said algorithm being done as follows:

from current PAS, PDS and luminance generated with said PAS and PDS, checking whether the current luminance is within a design range $LUMA_{MIN}$<current $LUMA<LUMA_{MAX}$;

if $LUMA_{MIN}$<current $LUMA<LUMA_{MAX}$, then no control is required;

otherwise, it is checked whether the time duration of the deviation with respect to the established range is larger than a design hysteresis time and if the current luminance is out of the design range for a time duration shorter than the defined hysteresis time, then no control is required;

otherwise, it is checked whether or not the current pulse amplitude setpoint PAS corresponds to a maximum value of intensity and, if not, then (912) the following calculation is performed: new_PAS=$(I_{frame}-I_{frame\_setpoint})\times$Gain_PAS, the new_PAS value being used to update said potentiometer;

if the current pulse amplitude setpoint PAS corresponds to a maximum value of intensity the pulse duration is adjusted as follows: new_PDS=$(I_{frame}-I_{frame\_setpoint})\times$Gain_PDS, the value of new_PDS being used to update said potentiometer;

at a pulse generator, receiving said pulse duration setpoint and generating from said pulse duration setpoint and from said strobe signal a pulsed signal having period $T_{frame}$ and having pulses of duration $T_{ON}$, $T_{ON}<<T_{frame}$, said duration $T_{ON}$ being obtained from said pulse duration setpoint and said strobe signal being used for synchronizing the pulses of duration $T_{ON}$ with the time instant at which the pixels in the image capture system start to capture an image;

calculating a reference voltage of duration $T_{ON}$ from said pulse amplitude setpoint, said reference voltage being used for obtaining a polarization current of said at least one LED;

providing a voltage enabling to provide a current Io' to said at least one LED at pulses of duration $T_{ON}$, said voltage being provided by a an RC network comprising at least one capacitor and a resistor, wherein said at least one capacitor works as a pulse energy storage means and said resistor regulates the charging speed of the a pulse energy storage means, said RC network being configured for the at least one capacitor to become fully charged in a time duration $T_{frame}-T_{ON}$, wherein $T_{frame}$ is the time period between two consecutive image frames captured by the image capture system.

17. The method of claim 16, further comprising providing homogeneous lighting to the area to be illuminated by means of a diffuser situated between the lighting system and the flow of fluid.

18. The method of claim 17, wherein the diffuser is situated closing off and sealing a hole made in the pipe through which the fluid flows.

19. The method of claim 16, further comprising focusing the captured images by means of a lens situated between the image capture system and the flow of fluid.

20. The method of claim 16, being capable of determining the presence and shape of objects having a largest dimension smaller than 20 μm.

\* \* \* \* \*